(12) United States Patent
Fidock

(10) Patent No.: US 7,052,895 B2
(45) Date of Patent: May 30, 2006

(54) PHOSPHODIESTERASE ENZYMES

(75) Inventor: Mark D. Fidock, Sandwich (GB)

(73) Assignee: Pfizer Inc., New York, NY (US)

( * ) Notice: Subject to any disclaimer, the term of this patent is extended or adjusted under 35 U.S.C. 154(b) by 34 days.

(21) Appl. No.: 10/781,102

(22) Filed: Feb. 18, 2004

(65) Prior Publication Data

US 2005/0048525 A1    Mar. 3, 2005

Related U.S. Application Data

(63) Continuation of application No. 09/663,481, filed on Sep. 15, 2000, now abandoned.

(60) Provisional application No. 60/177,326, filed on Jan. 21, 2000.

(30) Foreign Application Priority Data

Sep. 17, 1999   (GB) .................................. 9922125

(51) Int. Cl.
    *C12N 9/16*    (2006.01)
    *C12N 1/20*    (2006.01)
    *C12N 15/00*   (2006.01)
    *C07H 21/04*   (2006.01)

(52) U.S. Cl. ................ 435/196; 435/252.3; 435/320.1; 536/23.2

(58) Field of Classification Search ................ 435/196, 435/252.3, 320.1; 536/23.2; 530/300, 350
    See application file for complete search history.

(56) References Cited

U.S. PATENT DOCUMENTS

| 5,389,527 | A | * | 2/1995 | Beavo et al. ............... 435/69.1 |
| 5,885,834 | A | * | 3/1999 | Epstein ........................ 435/375 |
| 5,932,423 | A | | 8/1999 | Au-Young et al. ............. 435/6 |
| 5,932,465 | A | | 8/1999 | Loughney .................... 435/196 |
| 5,955,583 | A | | 9/1999 | Loughney .................... 435/196 |

OTHER PUBLICATIONS

Sequence alignment between Applicants' SEQ ID NO: 1 and Epstein's Accession No. AAW95110 (or SEQ ID No.:2).*
Sequence alignment between Applicants' SEQ ID NO: 1 and Beavo et al. Accession No. AAR69720 (or SEQ ID No. 27).*
Polli et al., *Proceedings of the Nathional Academy of Sciences of USA*, vol. 89, No. 22, pp. 11079-11083 (1992).
Reed, Tracey M. et al., *Mammalian Genome*, vol. 9, No. 7, pp. 571-576 (1998).
Yan. Chen et al., *Proceedings of the National Academy of Sciences of USA*, vol. 92, No. 21, pp. 9677-9681 (1995).
Yu, Josephine et al., *Cell Signal*, vol. 9, No. 7, pp. 519-529 (1997).

* cited by examiner

*Primary Examiner*—Tekchand Saidha
(74) *Attorney, Agent, or Firm*—Gregg C. Benson; Nicholas I. Slepchuk

(57) ABSTRACT

Amino acid sequences and nucleotide sequences relating to PDE1B2 are described. In a preferred aspect, the amino acid sequence comprises the sequence presented as SEQ ID No. 1.

8 Claims, 5 Drawing Sheets

Figure 1

```
HSPDE1A     ----MGSSATEIEELENTTFKYLTGEQTEKMWQRLKGI---------LRCLVKQLERGDV  47
HSPDE1B     MELSPRSPPEMLEESDCPSPLELKSAPSKKMWIKLRSL---------LRYMVKQLENGEI  51
HSPDE1C     ----MESPTKEIEEFESNSLKYLQPEQIEKIWLRLRGLRKYKKTSQRLRSLVKQLERGEA  56
             *..  :**  :   :      *     :*:* :*:..:          ** :*****.*:

HSPDE1A     NVVDLKKNIEYAASVLEAVYIDETRRLLDTEDELSDIQTDSVPSEVRDWLASTFTRKMGM 107
HSPDE1B     NIEELKKNLEYTASLLEAVYIDETRQILDTEDELQELRSDAVPSEVRDWLASTFTQQARA 111
HSPDE1C     SVVDLKKNLEYAATVLESVYIDETRRLLDTEDELSDIQSDAVPSEVRDWLASTFTRQMGM 116
             .:  :****:**:**.:**:*******:..******:.:::*:**************::

HSPDE1A     TKKKPEEKPKFRSIVHAVQAGIFVERMYRKTYHMVGLAYPAAVIVTLKDVDKWSFDVFAL 167
HSPDE1B     KGRRAEEKPKFRSIVHAVQAGIFVERMFRRTYTSVGPTYSTAVLNCLKNLDLWCFDVFSL 171
HSPDE1C     MLRRSDEKPRFKSIVHAVQAGIFVERMYRRTSNMVGLSYPPAVIEALKDVDKWSFDVFSL 176
             ::. :***:*:******************:*    **  :*..**:  **::*  *.****.*

HSPDE1A     NEASGEHSLKFMIYELFTRYDLINRFKIPVSCLITFAEALEVGYSKYKNPYHNLIHAADV 227
HSPDE1B     NQAADDHALRTIVFELLTRHNLISRFKIPTVFLMSFLDALETGYGKYKNPYHNQIHAADV 231
HSPDE1C     NEASGDHALKFIFYELLTRYDLISRFKIPISALVSFVEALEVGYSKHKNPYHNLMHAADV 236
             *:*: .:*:*:  :.  :.:**:**:.**.*****     *::*  :***.**.*.*.****** ; *****

HSPDE1A     TQTVHYIMLHTGIMHWLTELEILAMVFAAAIHDYEHTGTTNNFHIQTRSDVAILYNDRSV 287
HSPDE1B     TQTVHCFLLRTGMVHCLSEIELLAIIFAAAIHDYEHTGTTNSFHIQTKSECAIVYNDRSV 291
HSPDE1C     TQTVHYLLYKTGVANWLTELEIFAIIFSAAIHDYEHTGTTNNFHIQTRSDPAILYNDRSV 296
            *****  ::  :**: :  *:*:*::*:;*:************.*****:*: **:*****

HSPDE1A     LENHHVSAAYRLMQEEE-MNILINLSKDDWRDLRNLVIEMVLSTDMSGHFQQIKNIRNSL 346
HSPDE1B     LENHHISSVFRLMQDDE-MNIFINLTKDEFVELRALVIEMVLATDMSCHFQQVKTMKTAL 350
HSPDE1C     LENHHLSAAYRLLQDDEEMNILINLSKDDWREFRTLVIEMVMATDMSCHFQQIKAMKTAL 356
            *****:*::.:**:*:**   ***:***:**:;   ::* ******:;**** ****:*   :;..:*

HSPDE1A     QQPEGIDRAKTMSLILHAADISHPAKSWKLHYRWTMALMEEFFLQGDKEAELGLPFSPLC 406
HSPDE1B     QQLERIDKPKALSLLLHAADISHPTKQWLVHSRWTKALMEEFFRQGDKEAELGLPFSPLC 410
HSPDE1C     QQPEAIEKPKALSLMLHTADISHPAKAWDLHHRWTMSLLEEFFRQGDREAELGLPFSPLC 416
            **  *  *:;.*::**;:******:* *  :*  ***  :*:**** ***;*********

HSPDE1A     DRKSTMVAQSQIGFIDFIVEPTFSLLTDSTEKIVIPLIEEASKAETS-------SYVASS 459
HSPDE1B     DRTSTLVAQSQIGFIDFIVEPTFSVLTDVAEKSVQPLADEDSKSKNQP----SFQWRQPS 466
HSPDE1C     DRKSTMVAQSQVGFIDFIVEPTFTVLTDMTEKIVSPLIDETSQTGGTGQRRSSLNSISSS 476
            **.**;*****:*********:.***  :** ;** * **  :* *::             .  .*

HSPDE1A     STTIVGLHIA--------------DALRRSNTKGSMSDGSYSPDYSLAAVDLKSFKNNL 504
HSPDE1B     LDVEVGDPNP--------------DVVSFRSTWVKRIQENKQKWKERAASGITNQMS-- 509
HSPDE1C     DAKRSGVKTSGSEGSAPINNSVISVDYKSFKATWTEVVHINRERWRAKVPKEEKAKKEAE 536
                *    .          *  *    .  . .    ..  .  .

HSPDE1A     VDIIQQNKERWK--ELAAQEARTSSQKCEFIHQ--------------------------- 535
HSPDE1B     IDELSPCEEEAP--PSPAEDEHNQNGNLD------------------------------- 536
HSPDE1C     EKARLAAEEQQKEMEAKSQAEEGASGKAEBKKTSGETKNQVNGTRANKSDNPRGKNSKAEK 596
                .  :*.        ::   .  ..: *

HSPDE1A     -------------------------------------   (SEQ ID NO:22)
HSPDE1B     -------------------------------------   (SEQ ID NO:3)
HSPDE1C     SSGEQQQNGDFKDGKNKTDKKDHSNIGNDSKKTDDSQE 634 (SEQ ID NO:23)
```

Figure 3
PDE 1A Subtypes
Bovine 
Bovine 
Human 
Murine 
Human 

Figure 4A        N-terminal sequences of PDE1A splice variants
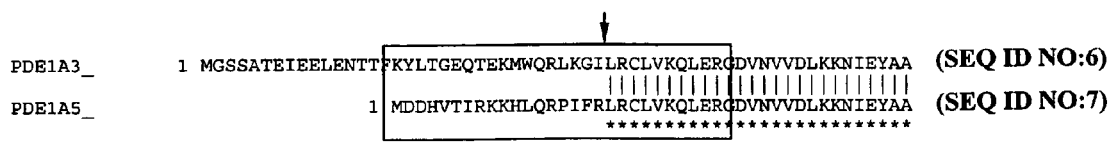
Figure 4B        N-terminal sequences of PDE1B splice variants
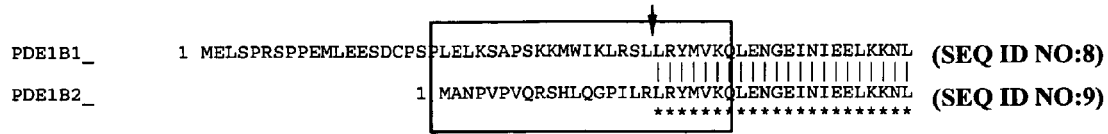
Figure 4C        Comparison of the CaM binding domains of the PDE1A1
                and PDE1B2 splice variants
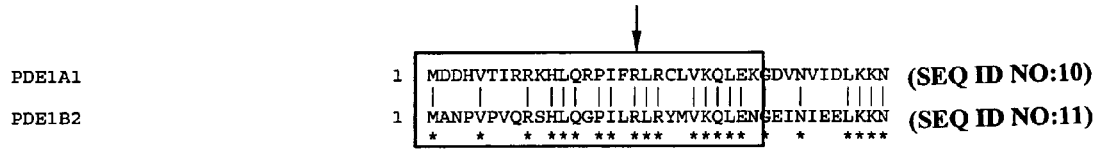
Figure 4D        Comparison of the CaM binding domains of the PDE1A2
                and PDE1B1 splice variants.
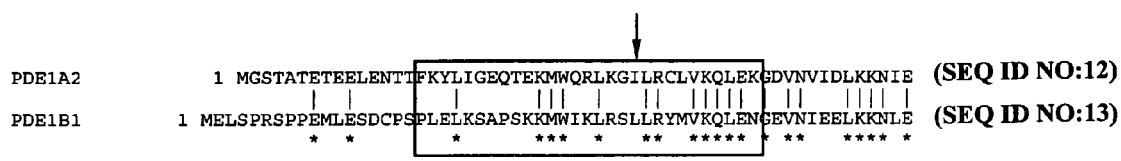

SEQUENCE LISTING

<160> NUMBER OF SEQ ID NOS: 21

<210> SEQ ID NO 1
<211> LENGTH: 516
<212> TYPE: PRT
<213> ORGANISM: Homo sapiens

<400> SEQUENCE: 1

Met Ala Asn Pro Val Pro Val Gln Arg Ser His Leu Gln Gly Pro Ile
1               5                   10                  15

Leu Arg Leu Arg Tyr Met Val Lys Gln Leu Glu Asn Gly Glu Ile Asn
            20                  25                  30

Ile Glu Glu Leu Lys Lys Asn Leu Glu Tyr Thr Ala Ser Leu Leu Glu
        35                  40                  45

Ala Val Tyr Ile Asp Glu Thr Arg Gln Ile Leu Asp Thr Glu Asp Glu
    50                  55                  60

Leu Gln Glu Leu Arg Ser Asp Ala Val Pro Ser Glu Val Arg Asp Trp
65                  70                  75                  80

Leu Ala Ser Thr Phe Thr Gln Gln Ala Arg Ala Lys Gly Arg Arg Ala
                85                  90                  95

Glu Glu Lys Pro Lys Phe Arg Ser Ile Val His Ala Val Gln Ala Gly
            100                 105                 110

Ile Phe Val Glu Arg Met Phe Arg Arg Thr Tyr Thr Ser Val Gly Pro
        115                 120                 125

Thr Tyr Ser Thr Ala Val Leu Asn Cys Leu Lys Asn Leu Asp Leu Trp
130                 135                 140

Cys Phe Asp Val Phe Ser Leu Asn Gln Ala Ala Asp Asp His Ala Leu
145                 150                 155                 160

Arg Thr Ile Val Phe Glu Leu Leu Thr Arg His Asn Leu Ile Ser Arg
                165                 170                 175

Phe Lys Ile Pro Thr Val Phe Leu Met Ser Phe Leu Asp Ala Leu Glu
            180                 185                 190

Thr Gly Tyr Gly Lys Tyr Lys Asn Pro Tyr His Asn Gln Ile His Ala
        195                 200                 205

Ala Asp Val Thr Gln Thr Val His Cys Phe Leu Leu Arg Thr Gly Met
    210                 215                 220

Val His Cys Leu Ser Glu Ile Glu Leu Leu Ala Ile Ile Phe Ala Ala
225                 230                 235                 240

Ala Ile His Asp Tyr Glu His Thr Gly Thr Thr Asn Ser Phe His Ile
                245                 250                 255

Gln Thr Lys Ser Glu Cys Ala Ile Val Tyr Asn Asp Arg Ser Val Leu
            260                 265                 270

Glu Asn His His Ile Ser Ser Val Phe Arg Leu Met Gln Asp Asp Glu
        275                 280                 285

Met Asn Ile Phe Ile Asn Leu Thr Lys Asp Glu Phe Val Glu Leu Arg
    290                 295                 300

Ala Leu Val Ile Glu Met Val Leu Ala Thr Asp Met Ser Cys His Phe
305                 310                 315                 320

Gln Gln Val Lys Thr Met Lys Thr Ala Leu Gln Gln Leu Glu Arg Ile
                325                 330                 335

Asp Lys Pro Lys Ala Leu Ser Leu Leu Leu His Ala Ala Asp Ile Ser
            340                 345                 350

His Pro Thr Lys Gln Trp Leu Val His Ser Arg Trp Thr Lys Ala Leu
         355                 360                 365

Met Glu Glu Phe Phe Arg Gln Gly Asp Lys Glu Ala Glu Leu Gly Leu
     370                 375                 380

Pro Phe Ser Pro Leu Cys Asp Arg Thr Ser Thr Leu Val Ala Gln Ser
385                 390                 395                 400

Gln Ile Gly Phe Ile Asp Phe Ile Val Glu Pro Thr Phe Ser Val Leu
                405                 410                 415

Thr Asp Val Ala Glu Lys Ser Val Gln Pro Leu Ala Asp Glu Asp Ser
             420                 425                 430

Lys Ser Lys Asn Gln Pro Ser Phe Gln Trp Arg Gln Pro Ser Leu Asp
         435                 440                 445

Val Glu Val Gly Asp Pro Asn Pro Asp Val Val Ser Phe Arg Ser Thr
     450                 455                 460

Trp Val Lys Arg Ile Gln Glu Asn Lys Gln Lys Trp Lys Glu Arg Ala
465                 470                 475                 480

Ala Ser Gly Ile Thr Asn Gln Met Ser Ile Asp Glu Leu Ser Pro Cys
                485                 490                 495

Glu Glu Glu Ala Pro Pro Ser Pro Ala Glu Asp Glu His Asn Gln Asn
             500                 505                 510

Gly Asn Leu Asp
         515

<210> SEQ ID NO 2
<211> LENGTH: 3091
<212> TYPE: DNA
<213> ORGANISM: Homo sapiens

<400> SEQUENCE: 2
gtcgacccac gcgtccggga ggaggaaggc aggggccaaa gaggaagttg tcccctcttg      60
ggggccctgg ggctcctggg gtcaggattt tgatactctg aagcaggaaa ctttgattcc     120
catggcaaac cctgttcctg ttcagaggag ccacctccag gcccccattc tcaggctgcg     180
ctacatggtg aagcagttgg agaatgggga gataaacatt gaggagctga gaaaaaatct     240
ggagtacaca gcttctctgc tggaagccgt ctacatagat gagacacggc aaatcttgga     300
cacggaggac gagctgcagg agctgcggtc agatgccgtg ccttcggagg tgcgggactg     360
gctggcctcc accttcaccc agcaggcccg ggccaaaggc cgccgagcag aggagaagcc     420
caagttccga agcattgtgc acgctgtgca ggctgggatc ttcgtggaac ggatgttccg     480
gagaacatac acctctgtgg cccccactta ctctactgcg gttctcaact gtctcaagaa     540
cctggatctc tggtgctttg atgtcttttc cttgaaccag gcagcagatg accatgccct     600
gaggaccatt gttttttgagt tgctgactcg gcataacctc atcagccgct tcaagattcc     660
cactgtgttt tgatgagtt tcctggatgc cttggagaca ggctatggga agtacaagaa     720
tccttaccac aaccagatcc acgcagccga tgttacccag acagtccatt gcttcttgct     780
ccgcacaggg atggtgcact gcctgtcgga gattgagctc ctggccatca tctttgctgc     840
agctatccat gattatgagc acacgggcac taccaacagc ttccacatcc agaccaagtc     900
agaatgtgcc atcgtgtaca atgatcgttt agtgctggag aatcaccaca tcagctctgt     960
tttccgattg atgcaggatg atgagatgaa catttcatc aacctcacca aggatgagtt    1020
tgtagaactc cgagccctgg tcattgagat ggtgttggcc acagacatgt cctgccattt    1080
ccagcaagtg aagaccatga gacagccctt gcaacagctg gagaggattg acaagcccaa    1140

```
ggccctgtct ctactgctcc atgctgctga catcagccac ccaaccaagc agtggttggt    1200
ccacagccgt tggaccaagg ccctcatgga ggaattcttc cgtcaggtg acaaggaggc     1260 agagttgggc ctgcccttt ctccactctg tgaccgcact tccactctag tggcacagtc    1320
tcagataggg ttcatcgact tcattgtgga gcccacattc tctgtgctga ctgacgtggc    1380
agagaagagt gttcagcccc tggcggatga ggactccaag tctaaaaacc agcccagctt    1440
tcagtggcgc cagccctctc tggatgtgga agtgggagac cccaaccctg atgtggtcag    1500
ctttcgttcc acctgggtca gcgcattca ggagaataag cagaaatgga aggaacgggc     1560
agcaagtggc atcaccaacc agatgtccat tgacgagctg tcccctgtg aagaagaggc     1620 cccccatcc cctgccgaag atgaacacaca ccagaatggg aatctggatt agccctgggg    1680
ctggcccagg tcttcattga gtccaaagtg tttgatgtca tcagcaccat ccatcaggac    1740
tggctccccc atctgctcca agggagcgtg gtcgtggaag aaacaaccca cctgaaggcc    1800
aaatgccaga gatttggggt tggggaaagg gcccctcccc acctgacacc cactgggtg    1860 cactttaatg ttccggcagc aagactgggg aacttcaggc tcccagtggt cactgtgccc    1920
atccctcagc ctctggattc tcttcatggc caggtggctg ccagggagcg gggagcttcc    1980
tggaggcttc ccagggcctt ggggaagggt cagagatgcc agcccctgg gacctccccc     2040 atcctttttg cctccaagtt tctaagcaat acatttggg ggttccctca gccccccacc     2100
ccagatctta gctggcaggt ctgggtgccc cttttcctcc cctgggaagg gctggaatag    2160
gatagaaagc tgggggtttt cagagcccta tgtgtgggga gggagtgga ttccttcagg     2220 gcatggtacc tttctaggat ctgggaatgg ggtggagagg acatcctctt cacccccagaa   2280 ttgcgctgct tcagccccat ctccagcctg atcctctgaa tcttccttcc ctcccttttct   2340 gatacagtga ctggggcaaa aggagccatt gtgaccaggg gctgcgggag gcctttcctg    2400
ggaccttcct tgggactggt ctgggcccct ggggcttgtc gcctgccctg agtccggagc    2460
cctttgcctc cttcctctcc cctggggctg ggaggctcca tccgaccaat gtctgtaaag    2520
tgctttgagg atctccccag caaagcacct tcagaatgta tcgacaccag ctgggttagg    2580
gtcaagggtg cctggggagg gtgagtaatc ctgcattgct aaaagagagg gtctgtcccc    2640
tcctctccac gtcccagaac tggcccagct gcaggcacta agaagctcct cccctgagac    2700
aagtgagggg tagtcggtga aaggcagatg gacaaggggc tcagggctgc tgccttcctg    2760
tcctctggag agaacccagc caggcgcggt gccccttcct ctcctcaggc tcctccttgc    2820
ccccaccttg ccccaggaaa ggccaaagtc caggtgactg ccctccttct ttcttgtaaa    2880
taccaaccat gcatttgtac agtgggccct gttcatgcga aatccacatc catggtctcc    2940
tagacctgct accctggtac ttccacccta ccccaccccg agaagggcag agacgcatgt    3000
gactcacccc tgcccttggt ttcccagacc cctgctatag ccagagaaca ataaagaagg    3060
gagaccagga aaaaaaaaaa aaaaaaaaa a                                     3091
```

<210> SEQ ID NO 3
<211> LENGTH: 536
<212> TYPE: PRT
<213> ORGANISM: Homo sapiens

<400> SEQUENCE: 3

Met Glu Leu Ser Pro Arg Ser Pro Pro Glu Met Leu Glu Glu Ser Asp
1               5                   10                  15

```
Cys Pro Ser Pro Leu Glu Leu Lys Ser Ala Pro Ser Lys Lys Met Trp
             20                  25                  30

Ile Lys Leu Arg Ser Leu Leu Arg Tyr Met Val Lys Gln Leu Glu Asn
         35                  40                  45

Gly Glu Ile Asn Ile Glu Glu Leu Lys Lys Asn Leu Glu Tyr Thr Ala
         50                  55                  60

Ser Leu Leu Glu Ala Val Tyr Ile Asp Glu Thr Arg Gln Ile Leu Asp
 65                  70                  75                  80

Thr Glu Asp Glu Leu Gln Glu Leu Arg Ser Asp Ala Val Pro Ser Glu
                     85                  90                  95

Val Arg Asp Trp Leu Ala Ser Phe Thr Gln Gln Ala Arg Ala Lys
                100                 105                 110

Gly Arg Ala Glu Glu Lys Pro Lys Phe Arg Ser Ile Val His Ala
            115                 120                 125

Val Gln Ala Gly Ile Phe Val Glu Arg Met Phe Arg Arg Thr Tyr Thr
        130                 135                 140

Ser Val Gly Pro Thr Tyr Ser Thr Ala Val Leu Asn Cys Leu Lys Asn
145                 150                 155                 160

Leu Asp Leu Trp Cys Phe Asp Val Phe Ser Leu Asn Gln Ala Ala Asp
                165                 170                 175

Asp His Ala Leu Arg Thr Ile Val Phe Glu Leu Leu Thr Arg His Asn
            180                 185                 190

Leu Ile Ser Arg Phe Lys Ile Pro Thr Val Phe Leu Met Ser Phe Leu
        195                 200                 205

Asp Ala Leu Glu Thr Gly Tyr Gly Lys Tyr Lys Asn Pro Tyr His Asn
210                 215                 220

Gln Ile His Ala Ala Asp Val Thr Gln Thr Val His Cys Phe Leu Leu
225                 230                 235                 240

Arg Thr Gly Met Val His Cys Leu Ser Glu Ile Glu Leu Leu Ala Ile
                245                 250                 255

Ile Phe Ala Ala Ala Ile His Asp Tyr Glu His Thr Gly Thr Thr Asn
            260                 265                 270

Ser Phe His Ile Gln Thr Lys Ser Glu Cys Ala Ile Val Tyr Asn Asp
        275                 280                 285

Arg Ser Val Leu Glu Asn His His Ile Ser Ser Val Phe Arg Leu Met
290                 295                 300

Gln Asp Asp Glu Met Asn Ile Phe Ile Asn Leu Thr Lys Asp Glu Phe
305                 310                 315                 320

Val Glu Leu Arg Ala Leu Val Ile Glu Met Val Leu Ala Thr Asp Met
                325                 330                 335

Ser Cys His Phe Gln Gln Val Lys Thr Met Lys Thr Ala Leu Gln Gln
            340                 345                 350

Leu Glu Arg Ile Asp Lys Pro Lys Ala Leu Ser Leu Leu Leu His Ala
        355                 360                 365

Ala Asp Ile Ser His Pro Thr Lys Gln Trp Leu Val His Ser Arg Trp
370                 375                 380

Thr Lys Ala Leu Met Glu Glu Phe Phe Arg Gln Gly Asp Lys Glu Ala
385                 390                 395                 400

Glu Leu Gly Leu Pro Phe Ser Pro Leu Cys Asp Arg Thr Ser Thr Leu
                405                 410                 415

Val Ala Gln Ser Gln Ile Gly Phe Ile Asp Phe Ile Val Glu Pro Thr
            420                 425                 430
```

```
Phe Ser Val Leu Thr Asp Val Ala Glu Lys Ser Val Gln Pro Leu Ala
            435                 440                 445

Asp Glu Asp Ser Lys Ser Lys Asn Gln Pro Ser Phe Gln Trp Arg Gln
            450                 455                 460

Pro Ser Leu Asp Val Glu Val Gly Asp Pro Asn Pro Asp Val Val Ser
465                 470                 475                 480

Phe Arg Ser Thr Trp Val Lys Arg Ile Gln Glu Asn Lys Gln Lys Trp
                485                 490                 495

Lys Glu Arg Ala Ala Ser Gly Ile Thr Asn Gln Met Ser Ile Asp Glu
            500                 505                 510

Leu Ser Pro Cys Glu Glu Ala Pro Pro Ser Pro Ala Glu Asp Glu
            515                 520                 525

His Asn Gln Asn Gly Asn Leu Asp
            530                 535

<210> SEQ ID NO 4
<211> LENGTH: 3112
<212> TYPE: DNA
<213> ORGANISM: Homo sapiens

<400> SEQUENCE: 4
```

| | | | | | |
|---|---|---|---|---|---|
| gtcgacccac | gcgtccgccc | acgcgtccgg | cctagagaca | ccggcctggc | tggtccacgc | 60 |
| cagccgcaga | ccgtggctga | gcatggagct | gtccccccgc | agtcctccgg | agatgctgga | 120 |
| ggagtcggat | tgcccgtcac | ccctggagct | gaagtcagcc | cccagcaaga | agatgtggat | 180 |
| taagcttcgg | tctctgctgc | gctacatggt | gaagcagttg | gagaatgggg | agataaacat | 240 |
| tgaggagctg | aagaaaaatc | tggagtacac | agcttctctg | ctggaagccg | tctacataga | 300 |
| tgagacacgc | caaatcttgg | acacggagga | cgagctgcag | gagctgcggt | cagatgccgt | 360 |
| gccttcggag | gtgcgggact | ggctggcctc | caccttcacc | cagcaggccc | gggccaaagg | 420 |
| ccgccgagca | gaggagaagc | ccaagttccg | aagcattgtg | cacgctgtgc | aggctgggat | 480 |
| cttcgtggaa | cggatgttcc | ggagaacata | cacctctgtg | gccccacctt | actctactgc | 540 |
| ggttctcaac | tgtctcaaga | acctggatct | ctggtgcttt | gatgtctttt | ccttgaacca | 600 |
| ggcagcagat | gaccatgccc | tgaggaccat | tgttttgag | ttgctgactc | ggcataacct | 660 |
| catcagccgc | ttcaagattc | ccactgtgtt | tttgatgagt | ttcctggatg | ccttggagac | 720 |
| aggctatggg | aagtacaaga | tccttacca | caaccagatc | cacgcagccg | atgttaccca | 780 |
| gacagtccat | tgcttcttgc | tccgcacagg | gatggtgcac | tgcctgtcgg | agattgagct | 840 |
| cctggccatc | atctttgctg | cagctatcca | tgattatgag | cacacgggca | ctaccaacag | 900 |
| cttccacatc | cagaccaagt | cagaatgtgc | catcgtgtac | aatgatcgtt | cagtgctgga | 960 |
| gaatcaccac | atcagctctg | ttttccgatt | gatgcaggat | gatgagatga | acattttcat | 1020 |
| caacctcacc | aaggatgagt | ttgtagaact | ccgagccctg | gtcattgaga | tggtgttggc | 1080 |
| cacagacatg | tcctgccatt | tccagcaagt | gaagaccatg | aagacagcct | tgcaacagct | 1140 |
| ggagaggatt | gacaagccca | aggccctgtc | tctactgctc | catgctgctg | acatcagcca | 1200 |
| cccaaccaag | cagtggttgg | tccacagccg | ttggaccaag | gccctcatgg | aggaattctt | 1260 |
| ccgtcagggt | gacaaggagg | cagagttggg | cctgccctt | tctccactct | gtgaccgcac | 1320 |
| ttccactcta | gtggcacagt | ctcagatagg | gttcatcgac | ttcattgtgg | agcccacatt | 1380 |
| ctctgtgctg | actgacgtgg | cagagaagag | tgttcagccc | ctggcggatg | aggactccaa | 1440 |
| gtctaaaaac | cagcccagct | ttcagtggcg | ccagccctct | ctggatgtgg | aagtgggaga | 1500 |

-continued

```
ccccaaccct gatgtggtca gctttcgttc cacctgggtc aagcgcattc aggagaacaa  1560
gcagaaatgg aaggaacggg cagcaagtgg catcaccaac cagatgtcca ttgacgagct  1620
gtccccctgt gaagaagagg ccccccatc ccctgccgaa gatgaacaca accagaatgg   1680
gaatctggat tagccctggg gctggcccag gtcttcattg agtccaaagt gtttgatgtc  1740
atcagcacca tccatcagga ctggctcccc catctgctcc aagggagcgt ggtcgtggaa  1800
gaaacaaccc acctgaaggc caaatgccag agatttgggg ttggggaaag ggcccctccc  1860
cacctgacac ccactggggt gcactttaat gttccggcag caagactggg gaacttcagg  1920
ctcccagtgg tcactgtgcc catccctcag cctctggatt ctcttcatgg ccaggtggct  1980
gccagggagc ggggagcttc ctggaggctt cccagggcct tggggaaggg tcagagatgc  2040 cagcccctg ggacctcccc catccttttt gcctccaagt ttctaagcaa tacattttgg    2100
gggttccctc agccccccac cccagatctt agctggcagg tctgggtgcc ccttttcctc   2160
ccctgggaag ggctggaata ggatagaaag ctggggttt tcagagccct atgtgtgggg    2220
aggggagtgg attccttcag ggcatggtac ctttctagga cctgggaatg gggtggagag   2280
gacatcctct tcaccccaga attgcgctgc ttcagcccca tctccagcct gatcctctga   2340
atcttccttc cctcccttc tgatatagtg actggggcaa aaggagccat tgtgaccagg    2400
ggctgcggga ggcctttcct gggaccttcc ttgggactgg tctgggcccc tggggcttgt   2460
cgcctgccct gagtccggag ccctttgcct ccttcctctc ccctgggct gggaggctcc    2520 atccgaccaa tgtctgtaaa gtgctttgag gatctcccca gcaaagcacc ttcagaatgt   2580
atcgacacca gctgggttag ggtcaagggt gcctggggag ggtgagtaat cctgcattgc   2640
taaaagagag ggtctgtccc ctcctctcca gtcccagaa ctggcccagc tgcaggcact    2700
aagaagctcc tcccctgaga caagtgaggg gtagtcggtg aaaggcagat ggacaagggg   2760
ctcagggctg ctgccttcct gtcctctgga gagaacccag ccaggcgcgg tgccccttcc   2820
tctcctcagg ctcctccttg cccccacctt gccccaggaa aggccaaagt ccaggtgact   2880
gccctccttc tttcttgtaa ataccaaccg tgcatttgta cagtgggccc tgttcatgcg   2940
aaatccacat ccatggtctc ctagacctgc taccctggta cttccaccct accccacccc   3000
gagaagggca gagacgcatg tgactcaccc ctgcccttgg tttcccagac ccctgctaca   3060
gccagagaac aataaagaag ggagaccagg aaaaaaaaaa aaaaaaaaa aa           3112
```

<210> SEQ ID NO 5
<211> LENGTH: 24
<212> TYPE: PRT
<213> ORGANISM: Homo sapiens

<400> SEQUENCE: 5

Met Ala Asn Pro Val Pro Val Gln Arg Ser His Leu Gln Gly Pro Ile
1               5                   10                  15

Leu Arg Leu Arg Tyr Met Val Lys
            20

<210> SEQ ID NO 6
<211> LENGTH: 60
<212> TYPE: PRT
<213> ORGANISM: Homo sapiens

<400> SEQUENCE: 6

Met Gly Ser Ser Ala Thr Glu Ile Glu Glu Leu Glu Asn Thr Thr Phe
1               5                   10                  15

```
Lys Tyr Leu Thr Gly Glu Gln Thr Glu Lys Met Trp Gln Arg Leu Lys
            20                  25                  30

Gly Ile Leu Arg Cys Leu Val Lys Gln Leu Glu Arg Gly Asp Val Asn
            35                  40                  45

Val Val Asp Leu Lys Lys Asn Ile Glu Tyr Ala Ala
 50                  55                  60

<210> SEQ ID NO 7
<211> LENGTH: 44
<212> TYPE: PRT
<213> ORGANISM: Homo sapiens

<400> SEQUENCE: 7

Met Asp Asp His Val Thr Ile Arg Lys Lys His Leu Gln Arg Pro Ile
1               5                   10                  15

Phe Arg Leu Arg Cys Leu Val Lys Gln Leu Glu Arg Gly Asp Val Asn
            20                  25                  30

Val Val Asp Leu Lys Lys Asn Ile Glu Tyr Ala Ala
            35                  40

<210> SEQ ID NO 8
<211> LENGTH: 60
<212> TYPE: PRT
<213> ORGANISM: Homo sapiens

<400> SEQUENCE: 8

Met Glu Leu Ser Pro Arg Ser Pro Glu Met Leu Glu Glu Ser Asp
1               5                   10                  15

Cys Pro Ser Pro Leu Glu Leu Lys Ser Ala Pro Ser Lys Lys Met Trp
            20                  25                  30

Ile Lys Leu Arg Ser Leu Leu Arg Tyr Met Val Lys Gln Leu Glu Asn
            35                  40                  45

Gly Glu Ile Asn Ile Glu Glu Leu Lys Lys Asn Leu
 50                  55                  60

<210> SEQ ID NO 9
<211> LENGTH: 40
<212> TYPE: PRT
<213> ORGANISM: Homo sapiens

<400> SEQUENCE: 9

Met Ala Asn Pro Val Pro Val Gln Arg Ser His Leu Gln Gly Pro Ile
1               5                   10                  15

Leu Arg Leu Arg Tyr Met Val Lys Gln Leu Glu Asn Gly Glu Ile Asn
            20                  25                  30

Ile Glu Glu Leu Lys Lys Asn Leu
            35                  40

<210> SEQ ID NO 10
<211> LENGTH: 39
<212> TYPE: PRT
<213> ORGANISM: Homo sapiens

<400> SEQUENCE: 10

Met Asp Asp His Val Thr Ile Arg Arg Lys His Leu Gln Arg Pro Ile
1               5                   10                  15

Phe Arg Leu Arg Cys Leu Val Lys Gln Leu Glu Lys Gly Asp Val Asn
            20                  25                  30

Val Ile Asp Leu Lys Lys Asn
            35
```

<210> SEQ ID NO 11
<211> LENGTH: 39
<212> TYPE: PRT
<213> ORGANISM: Homo sapiens

<400> SEQUENCE: 11

Met Ala Asn Pro Val Pro Val Gln Arg Ser His Leu Gln Gly Pro Ile
1               5                   10                  15

Leu Arg Leu Arg Tyr Met Val Lys Gln Leu Glu Asn Gly Glu Ile Asn
            20                  25                  30

Ile Glu Glu Leu Lys Lys Asn
            35

<210> SEQ ID NO 12
<211> LENGTH: 57
<212> TYPE: PRT
<213> ORGANISM: Homo sapiens

<400> SEQUENCE: 12

Met Gly Ser Thr Ala Thr Glu Thr Glu Leu Glu Asn Thr Thr Phe
1               5                   10                  15

Lys Tyr Leu Ile Gly Glu Gln Thr Glu Lys Met Trp Gln Arg Leu Lys
            20                  25                  30

Gly Ile Leu Arg Cys Leu Val Lys Gln Leu Glu Lys Gly Asp Val Asn
            35                  40                  45

Val Ile Asp Leu Lys Lys Asn Ile Glu
    50                  55

<210> SEQ ID NO 13
<211> LENGTH: 60
<212> TYPE: PRT
<213> ORGANISM: Homo sapiens

<400> SEQUENCE: 13

Met Glu Leu Ser Pro Arg Ser Pro Glu Met Leu Glu Ser Asp Cys
1               5                   10                  15

Pro Ser Pro Leu Glu Leu Lys Ser Ala Pro Ser Lys Lys Met Trp Ile
            20                  25                  30

Lys Leu Arg Ser Leu Leu Arg Tyr Met Val Lys Gln Leu Glu Asn Gly
            35                  40                  45

Glu Val Asn Ile Glu Glu Leu Lys Lys Asn Leu Glu
    50                  55                  60

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14
cagtaacaga tgagctgc                                                     18

<210> SEQ ID NO 15
<211> LENGTH: 16
<212> TYPE: DNA
<213> ORGANISM: Artificial
<220> FEATURE:
<223> OTHER INFORMATION: primer

<400> SEQUENCE: 15

```
gtattccttt caggcg                                                   16

<210> SEQ ID NO 16
<211> LENGTH: 16
<212> TYPE: DNA
<213> ORGANISM: Artificial
<220> FEATURE:
<223> OTHER INFORMATION: primer

<400> SEQUENCE: 16
cacatttcct ctctgg                                                   16

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
gggtctttgg agatgtttct tcc                                           23

<210> SEQ ID NO 18
<211> LENGTH: 18
<212> TYPE: DNA
<213> ORGANISM: Artificial
<220> FEATURE:
<223> OTHER INFORMATION: primer

<400> SEQUENCE: 18
ctgagcatgg agctgtcc                                                 18

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
cagagaccga agcttaatcc                                               20

<210> SEQ ID NO 20
<211> LENGTH: 18
<212> TYPE: DNA
<213> ORGANISM: Artificial
<220> FEATURE:
<223> OTHER INFORMATION: primer

<400> SEQUENCE: 20
ccaaagagga agttgtcc                                                 18

<210> SEQ ID NO 21
<211> LENGTH: 15
<212> TYPE: DNA
<213> ORGANISM: Artificial
<220> FEATURE:
<223> OTHER INFORMATION: primer

<400> SEQUENCE: 21
gcagcctgac aatgg                                                    15
```

PHOSPHODIESTERASE ENZYMES

This application is a continuation application of U.S. patent application Ser. No. 09/663,481 filed on Sep. 15, 2000, now abandoned, which claims the benefit of U.S. Provisional Application No. 60/177,326, filed on Jan. 21, 2000. This application claims priority under 35 U.S.C. §120 on U.S. patent application Ser. No. 09/663,481, filed on Sep. 15, 2000 and Provisional Patent Application No. 60/177,326, filed on Jan. 20, 2000. Priority is also claimed under 35 U.S.C. §119 on Great Britain Patent Application No. 9922125.1, filed on Sep. 17, 1999.

BACKGROUND OF THE PRESENT INVENTION

The present invention relates to an enzyme. The present invention also relates to a nucleotide sequence encoding same.

In particular, the present invention relates to a novel nucleic acid sequence encoding a novel phosphodiesterase enzyme.

The present invention also relates to the use of the novel nucleic acid and amino acid sequences in the diagnosis and treatment of disease.

The present invention also relates to the use of the novel nucleic acid and amino acid sequences to evaluate and/or to screen for agents that can modulate phosphodiesterase activity.

The present invention further relates to genetically engineered host cells that comprise or express the novel nucleic acid and amino acid sequences to evaluate and/or to screen for agents that can modulate phosphodiesterase activity.

BACKGROUND ART

Cyclic nucleotides, such as cAMP and cGMP, are important intracellular second messengers. Cyclic nucleotide phosphodiesterases—otherwise known as PDEs—are a family of enzymes that catalyse the degradation of cyclic nucleotides and, in doing so, are one of the cellular components that regulate the concentration of cyclic nucleotides.

In recent years, at least seven PDE enzymes (such as PDEI–PDEVII), as well as many subtypes of these enzymes, have been defined based on substrate affinity and cofactor requirements (Beavo J A and Reifsnyder D H, Trends Pharmacol. Sci. 11:150 [1990]; Beavo J, In: Cyclic Nucleotide Phosphodiesterases: Structure, Regulation and Drug Action., Beavo J and Housley M D (Eds.). Wiley:Chichester, pp. 3–15 [1990]). Examples of PDEs include: PDEI which is a $Ca^{2+}$/Calmodulin-dependent PDE; PDEII which is a cGMP stimulated PDE; PDEIII which is a cGMP inhibited PDE; PDEIV which is a high affinity cAMP-specific PDE; and PDEV which is a cGMP specific PDE.

Each PDE family may contain two or more isoforms (i.e. there may be two or more PDE isoenzymes). By way of example, mammalian PDE IV, the homologue of the *Drosophila* Dunce gene (Chen C N et al., Proc. Nat. Acad. Sci. (USA) 83:9313 [1986]), is known to have four isoforms in the rat (Swinnen J V et al., Proc. Nat. Acad. Sci. (USA) 86:5325 [1989]). Human PDEs are also known to occur as isoforms and have splice variants. For example, the cloning of one human isoform of PDEIV from monocytes was reported in 1990 (Livi G P et al., Mol. Cell. Bio., 10:2678 [1990]). By way of further example, other workers have independently cloned three splice variants of PDEIV, which are now designated hPDEIV-B1, hPDEIV-B2, and hPDEIV-B3.

Teachings on cyclic nucleotide phosphodiesterases can also be found in U.S. Pat. Nos. 5,932,423 and 5,932,465.

Teachings on a further cyclic nucleotide phosphodiesterase—namely CN PCDE8—can be found in WO-A-97/35989. According to WO-A-97/35989, CN PCDE8 has two isozymes—which were designated CN PCDE8A and CN PCDE8B. The term "isozyme" is sometimes referred to in the art as "isoform".

According to WO-A-97/35989, many inhibitors of different PDEs have been identified and some have undergone clinical evaluation. For example, PDEIII inhibitors are being developed as antithrombotic agents, as antihypertensive agents and as cardiotonic agents useful in the treatment of congestive heart failure. Rolipram, a PDEIII inhibitor, has been used in the treatment of depression and other inhibitors of PDEIII are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al 1995 AIDS 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al, 1995 Nat Med 1:244–248) and may be effective in the treatment of tardive dyskinesia (Sasaki et al, 1995 Eur J Phamacol 282:71–76).

According to WO-A-97/35989, there are also non-specific PDE inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immuno modulatory capacity in the treatment of respiratory diseases (Banner et al 1995 Respir J 8:996–1000) where it is thought to act by inhibiting both CN PDE cAMP and cGMP hydrolysis (Banner et al 1995 Monaldi Arch Chest Dis 50:286–292). Pentoxifylline, also known to block TNF-alpha production, may inhibit HIV-1 replication (Angel et al supra). A list of CN PDE inhibitors is given in Beavo 1995 supra.

It has been suggested that selective inhibitors of PDEs, in addition to their isozymes and their subtypes, will lead to more effective therapy with fewer side effects. For example, see the teachings in the reviews of Wieshaar R E et al, (J. Med. Chem., 28:537 [1985]), Giembycz M A (Biochem. Pharm., 43:2041 [1992]) and Lowe J A and Cheng J B (Drugs of the Future, 17:799–807 [1992]).

Thus, for some applications it is desirable to have a selective inhibition of an individual type of PDE. Hence, the cloning and expression of a novel PDE would greatly aid the discovery of selective inhibitors.

SUMMARY ASPECTS OF THE PRESENT INVENTION

Aspects of the present invention are presented in the claims and in the following commentary.

In a broad aspect, the present invention relates to novel amino acid sequences. In this regard, we have identified a specific novel amino acid sequence and it is to be understood that the invention covers that sequence as well as novel variants, fragments, derivatives, homologues thereof.

In another broad aspect, the present invention relates to novel nucleic acid sequences. In this regard, we have identified a specific novel nucleic acid sequence and it is to be understood that the invention covers that sequence as well as novel variants, fragments, derivatives, homologues thereof.

BRIEF DESCRIPTION OF THE FIGURES

FIG. 1 presents a multiple sequence alignment of the PDE1 gene family.

FIG. 3 presents schematic diagrams of PDE1A subtypes for bovine, human and murine species cDNAs.

FIGS. 4A to 4D presents a Clustalus alignment of the differential N-terminal regions of PDE1A and PDE1B splice variants.

Figure 2:
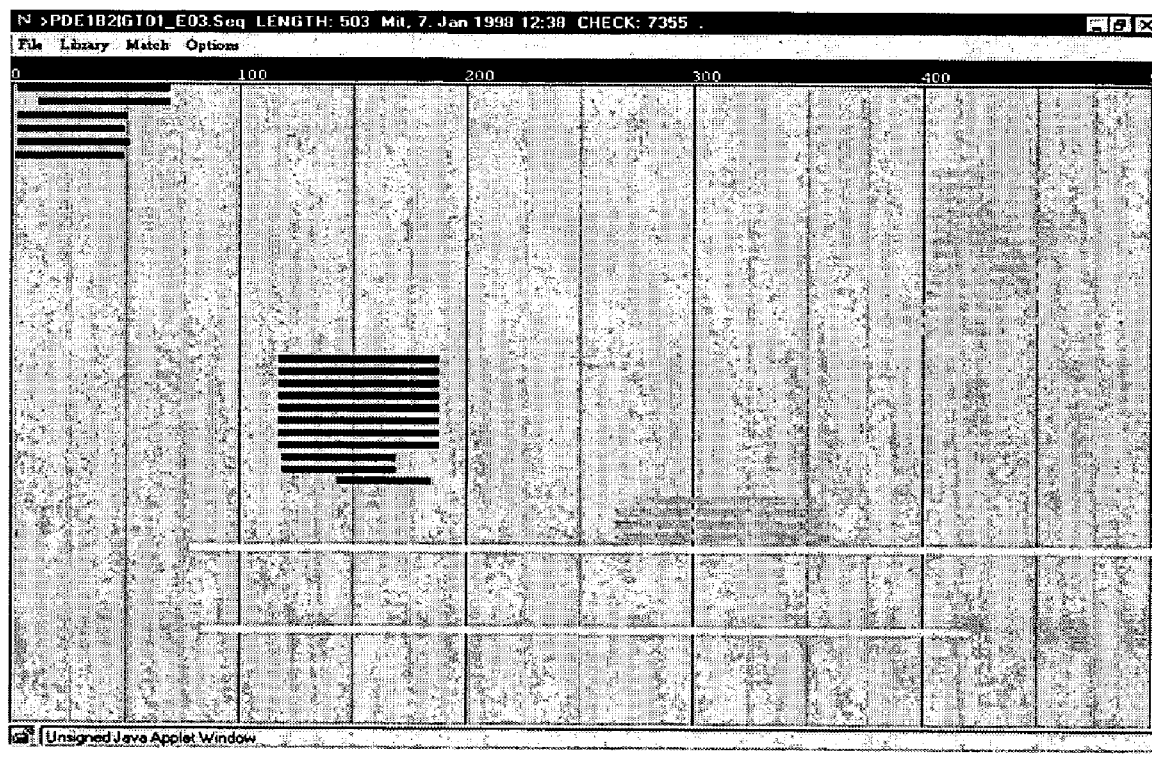
FIG. 2 presents an image of a Java Applet for PDE sequences.

Thus, in brief, some aspects of the present invention relate to:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of present invention; a tissue comprising or capable of expressing the sequences of the present invention; an organ comprising or capable of expressing the sequences of the present invention; a transformed host comprising or capable of expressing the sequences of the present invention; a transformed organism comprising or capable of expressing the sequences of the present invention. The present invention also encompasses methods of expressing the same, such as expression in a micro-organism; including methods for transferring same.

For ease of reference, aspects of the present invention are now discussed under appropriate section headings. However, the teachings under each section are not necessarily limited to each particular section.

In the following commentary references to "nucleotide sequence of the present invention" and "amino acid sequence of the present invention" refer respectively to any one or more of the nucleotide sequences presented or discussed herein and to any one or more of the amino acid sequences presented or discussed herein. Also, and as used herein, "amino acid sequence" refers to peptide or protein sequences and may refer to portions thereof. In addition, the term "amino acid sequence of the present invention" is synonymous with the phrase "polypeptide sequence of the present invention". Also, the term "nucleotide sequence of the present invention" is synonymous with the phrase "polynucleotide sequence of the present invention".

DETAILED ASPECTS OF THE PRESENT INVENTION

According to one aspect of the present invention there is provided an amino acid sequence comprising the sequence presented as SEQ ID NO:1, or a variant, homologue, fragment or derivative thereof, wherein the amino acid sequence is capable of displaying PDE activity.

Without wishing to be bound by theory, we believe that the PDE of the present invention may have a calmodulin binding site, which may be distinct from the catalytic site.

Preferably, the amino acid sequence of the present invention has a calmodulin binding site, which may be distinct from the catalytic site.

For convenience, we now present a Table indicating the codes used for the amino acids.

| AMINO ACID | THREE LETTER ABBREVIATION | ONE LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

For convenience, the PDE of the present invention is sometimes referred to as PDE1B2. If the PDE is obtainable from a human, then typically it is referred to as HMPDE1B2 or HSPDE1B2.

We believe that PDE of the present invention is a splice variant of PDE1.

The PDE of the present invention is capable of catalysing the degradation of cAMP and/or cGMP.

For SEQ ID NO:1 any one or more of the amino acids may be an analogue thereof.

The term "analogue" as used herein means a sequence having a sequence similar to that of SEQ ID No:1 but wherein non-detrimental (i.e. not detrimental to enzymatic activity) amino acid substitutions or deletions have been made.

According to a second aspect of the present invention there is provided a nucleotide sequence encoding the amino acid sequence of the present invention.

Preferably, the nucleotide sequence comprises the sequence presented as SEQ ID NO:2, or a variant, homologue, fragment or derivative thereof, wherein the nucleotide sequence codes for an amino acid sequence that is capable of displaying PDE activity.

According to a third aspect of the present invention there is provided a nucleotide sequence that is capable of hybridising to the nucleotide sequence according to the present invention, or a sequence that is complementary thereto.

According to a fourth aspect of the present invention there is provided a nucleotide sequence that is capable of hybridising to the nucleotide sequence according to the third aspect of the present invention, or a sequence that is complementary thereto.

According to a fifth aspect of the present invention there is provided a vector comprising the nucleotide sequence according to the present invention.

According to a sixth aspect of the present invention there is provided a host cell into which has been incorporated the nucleotide sequence according to the present invention.

According to a seventh aspect of the present invention there is provided an assay method for identifying an agent that can affect PDE1B2 activity or expression thereof, the assay method comprising contacting an agent with an amino acid according to the present invention or a nucleotide sequence according to the present invention; and measuring the activity or expression of PDE1B2; wherein a difference between a) PDE activity or expression in the absence of the agent and b) PDE activity or expression in the presence of the agent is indicative that the agent can affect PDE1B2 activity or expression.

Preferably the assay is to screen for agents useful in the treatment of a cardiovascular disorder, a GI disorder, and/or disorders found in any any one or more of the cardiovascular system, the GI system, spleen.

According to an eighth aspect of the present invention there is provided a process comprising the steps of: (a) performing the assay according to the present invention; (b) identifying one or more agents that do affect PDE1B2 activity or expression; and (c) preparing a quantity of those one or more identified agents.

According to a ninth aspect of the present invention there is provided a method of affecting in vivo PDE1B2 activity or expression with an agent; wherein the agent is capable of affecting PDE1B2 activity or expression in an in vitro assay method; wherein the in vitro assay method is the assay method of the present invention.

According to a tenth aspect of the present invention there is provided the use of an agent in the preparation of a pharmaceutical composition for the treatment of a disease or condition associated with PDE1B2, the agent is capable of having an effect on the activity or expression of PDE when assayed in vitro by the assay method of the present invention.

According to an eleventh aspect of the present invention there is provided an enzyme capable of having an immunological reaction with an antibody raised against PDE1B2.

According to a twelfth aspect of the present invention there is provided a nucleotide sequence coding for a PDE, wherein the nucleotide sequence is obtainable from NCIMB 41026.

According to a thirteenth aspect of the present invention there is provided a PDE wherein the PDE is expressable from a nucleotide sequence obtainable from NCIMB 41026.

According to a fourteenth aspect of the present invention there is provided the use of an agent which has an effect on the activity of PDE1B2 or the expression thereof in the preparation of a pharmaceutical composition for the treatment of a disease or condition associated with PDE1B2 .

According to a further aspect of the present invention there is provided a nucleotide sequence selected from:
(a) the nucleotide sequence presented as SEQ ID NO:2;
(b) a nucleotide sequence that is a variant, homologue, derivative or fragment of the nucleotide sequence presented as SEQ ID NO:2;
(c) a nucleotide sequence that is the complement of the nucleotide sequence set out as SEQ ID NO:2;
(d) a nucleotide sequence that is the complement of a variant, homologue, derivative or fragment of the nucleotide sequence presented as SEQ ID NO:2;
(e) a nucleotide sequence that is capable of hybridising to the nucleotide sequence set out as SEQ ID NO:2;
(f) a nucleotide sequence that is capable of hybridising to a variant, homologue, derivative or fragment of the nucleotide sequence presented as SEQ ID NO:2;
(g) a nucleotide sequence that is the complement of a nucleotide sequence that is capable of hybridising to the nucleotide sequence set out as SEQ ID NO:2;
(h) a nucleotide sequence that is the complement of a nucleotide sequence that is capable of hybridising to a variant, homologue, derivative or fragment of the nucleotide sequence presented as SEQ ID NO:2;
(i) a nucleotide sequence that is capable of hybridising to the complement of the nucleotide sequence set out as SEQ ID NO:2;
(j) a nucleotide sequence that is capable of hybridising to the complement of a variant, homologue, derivative or fragment of the nucleotide sequence presented as SEQ ID NO:2;
(k) a nucleotide sequence which is degenerate as a result of the genetic code to the nucleotides defined in (a), (b), (c), (d), (e), (f), (g), (h), (i), or (j);
(l) a nucleotide sequence comprising any one of (a), (b), (c), (d), (e), (f), (g), (h), (i), (j) and/or (k).

Other aspects of the present invention are now presented below.

An isolated nucleotide sequence or an isolated protein sequence according to the present invention.

A substantially pure nucleotide sequence or a substantially pure protein sequence according to the present invention.

An assay method for identifying an agent that can affect the expression pattern of the nucleotide sequence of the present invention or the activity of the expression product thereof, the assay-method comprising: exposing the nucleotide sequence of the present invention or the expression product ("EP") thereof with an agent; determining whether the agent modulates (such as affects the expression pattern or activity) the nucleotide sequence of the present invention or the expression product thereof.

An agent identified by the assay method of the present invention.

An agent identified by the assay method of the present invention, which agent has hitherto been unknown to have a PDE modulation effect in accordance with the present, invention.

A process comprising the steps of: (a) performing the assay of the present invention; (b) identifying one or more agents that affect the, expression pattern of the nucleotide sequence of the present invention or the activity of the expression product thereof; (c) preparing a quantity of those one or more identified agents.

A process comprising the steps of: (a) performing the assay according to the present invention; (b) identifying one or more agents that affect the expression pattern of the nucleotide sequence of the present invention or the activity of the expression product thereof; (c) preparing a pharmaceutical composition comprising one or more identified agents.

A process comprising the steps of: (a) performing the assay according to the present invention; (b) identifying one or more agents that affect the expression pattern of the nucleotide sequence of the present invention or the activity of the expression product thereof; (c) modifying one or more identified agents to cause a different effect on the expression pattern of the nucleotide sequence of the present invention or the activity of the expression product thereof.

Use of an agent identified by an assay according to the present invention in the manufacture of a medicament which affects the expression pattern of the nucleotide sequence of the present invention or the activity of the expression product thereof.

A method of treating a target (which target can be a mammal, preferably a human), which method comprises delivering (such as administering or exposing) to the target an effective amount of an agent capable of modulating the expression pattern of the nucleotide sequence of the present invention or the activity of the expression product thereof.

A method of treating a target (which target can be a mammal, preferably a human), which method comprises delivering (such as administering or exposing) to the target an effective amount of an agent identified by an assay according to the present invention.

A method of inducing an immunological response in a subject, the method comprising administering to the subject the nucleotide sequence of the present invention or the expression product thereof.

PDE1B2

As explained above, the present invention relates to a novel PDE enzyme—which we have called PDE1B2—and to a nucleotide sequence encoding same. The present invention also relates to the use of the novel nucleic acid and amino acid sequences in the diagnosis and treatment of disease. The present invention also relates to the use of the novel nucleic acid and amino acid sequences to evaluate and/or to screen for agents that can modulate phosphodiesterase activity. The present invention further relates to genetically engineered host cells that comprise or express the novel nucleic acid and amino acid sequences to evaluate and/or to screen for agents that can modulate phosphodiesterase activity.

PDE1B2 is believed to be present in, and obtainable from, a variety of sources.

By way of example, PDE1B2 is found in any one or more of the cardiovascular system, the GI system, spleen.

We also believe that PDE1B2 is also present in a number of other sources—such as for example: murine, rat, bovine, ovine, porcine, and equine.

Preferably, the present invention covers mammalian PDE1B2 which includes but is not limited to any of the above sources.

More preferably, the present invention covers human PDE1B2.

The PDE1B2 may be the same as the naturally occurring form—for this aspect, preferably the PDE1B2 is the non-native amino acid sequence (i.e. it is not present in its natural environment)—or is a variant, homologue, fragment or derivative thereof. In addition, or in the alternative, the PDE1B2 is isolated PDE1B2 and/or purified PDE1B2. The PDE1B2 can be obtainable from or produced by any suitable source, whether natural or not, or it may be synthetic, semi-synthetic or recombinant.

The PDE1B2 coding sequence may be the same as the naturally occurring form—for this aspect, preferably the PDE1B2 coding sequence is the non-native nucleotide sequence (i.e. it is not present in its natural environment)—or is a variant, homologue, fragment or derivative thereof. In addition, or in the alternative, the PDE1B2 coding sequence is an isolated PDE1B2 coding sequence and/or a purified PDE1B2 coding sequence. The PDE1B2 coding sequence can be obtainable from or produced by any suitable source, whether natural or not, or it may be synthetic, semi-synthetic or recombinant.

PDE1B2 and/or its coding sequence and/or a sequence capable of hybridising thereto is/are useful for testing the selectivity of drug candidates between different PDEs.

PDE1B2 is believed to be able to catalyse the conversion of cGMP to GMP and/or cAMP to AMP.

cGMP is the messenger in the male erectile response. Accordingly, inhibiting the activity of PDE1B2 may cause an increase the concentration of cGMP present and so may enhance the male erectile response.

Thus, PDE1B2 and/or its coding sequence and/or a sequence capable of hybridising thereto may be useful for screening drug candidates for the treatment of male erectile dysfunction. In addition, it is believed that PDE1B2 and/or its coding sequence and/or a sequence capable of hybridising thereto may be useful for screening drug candidates for the treatment of female sexual dysfunction.

Preferred aspects of the present invention include a recombinant PDE1B2 enzyme and a recombinant nucleotide sequence encoding a PDE1B2 enzyme.

Preferably the recombinant PDE1B2 enzyme and/or the recombinant nucleotide sequence of the present invention are a recombinant mammalian PDE1B2 enzyme and/or a recombinant mammalian nucleotide sequence.

Preferably the recombinant PDE1B2 enzyme and/or the recombinant nucleotide sequence of the present invention are a recombinant human PDE1B2 enzyme and/or a recombinant human nucleotide sequence.

Either or both of the nucleotide sequence coding for PDE1B2 or the enzyme PDE1B2 itself may be used to screen for agents that can affect PDE1B2 activity. In particular, the nucleotide sequence coding for PDE1B2 or PDE1B2 itself may be used to screen for agents that can inhibit PDE1B2 activity. In addition, the nucleotide sequence coding for PDE1B2 or the enzyme PDE1B2 itself may be used to screen for agents that selectively affect PDE1B2 activity, such as selectively inhibit PDE1B2 activity.

Furthermore, the nucleotide sequence coding for PDE1B2 or a sequence that is complementary thereto may also be used in assays to detect the presence of PDE1B2 coding sequences in human cells. These assays would provide information regarding the tissue distribution of this enzyme and its biological relevance with respect to particular disease states.

The present invention also covers antibodies to PDE1B2 (including a derivative, fragment, homologue or variant thereof). The antibodies for PDE1B2 may be used in assays to detect the presence of PDE1B2 in human cells. These assays would provide information regarding the tissue distribution of this enzyme and its biological relevance with respect to particular disease states.

In particular, any one or more of the PDE1B2 isozymes, the nucleotide sequences coding for same, the nucleotide sequences that are complementary to same, and the antibodies directed to same may be used in assays to screen for agents that selectively affect one of the isozymes. These assays would provide information regarding the tissue distribution of each of the isozymes and to provide information regarding the biological relevance of each of the isozymes with respect to particular disease states. These assays would also allow workers to test for and identify agents that are useful to affect the expression of or activity of PDE1B2—such as in a particular tissue or in a particular disease state.

Polypeptide of the Present Invention

The term "polypeptide"—which is interchangeable with the term "protein"—includes single-chain polypeptide molecules as well as multiple-polypeptide complexes where individual constituent polypeptides are linked by covalent or non-covalent means.

Preferably, the polypeptide of the present invention is a single-chain polypeptide.

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification or by the addition of a signal sequence to promote their secretion from a cell as discussed below.

Polypeptides of the present invention may be produced by synthetic means (e.g. as described by Geysen et al., 1996) or recombinantly, as described below.

In a preferred embodiment, the amino acid sequence per se the present invention does not cover the native PDE1B2 according to the present invention when it is in its natural environment and when it has been expressed by its native nucleotide coding sequence which is also in its natural environment and when that nucleotide sequence is under the control of its native promoter which is also in its natural environment. For ease of reference, we have called this preferred embodiment the "non-native amino acid sequence".

The terms "variant", "homologue" or "fragment" in relation to the amino acid sequence for the enzyme of the present invention include any substitution of, variation of, modification of, replacement of, deletion of or addition of one (or more) amino acid from or to the sequence providing the resultant enzyme has PDE1B2 activity, preferably being at least as biologically active as the enzyme shown in the attached sequence listings. In particular, the term "homologue" covers homology with respect to structure and/or function. With respect to sequence homology, preferably there is at least 75%, more preferably at least 85%, more preferably at least 90% homology to the sequence shown as SEQ ID NO:1. More preferably there is at least 95%, more preferably at least 98%, homology to the sequence shown as SEQ ID NO:1.

Preferably, the variant, homologue or fragment of the present invention comprises a nucleotide sequence that encodes for at least 5 contiguous amino acids, preferably at least 10 contiguous amino acids, preferably at least 15 contiguous amino acids, preferably at least 20 contiguous amino acids, preferably at least 21 contiguous amino acids, preferably at least 22 contiguous amino acids, preferably at least 23 contiguous amino acids, preferably at least 24 contiguous amino acids, of the following N terminal sequence:
MANPVPVQRSHLQGPILRLRYMVK (SEQ ID NO:5)

Typically, for the variant, homologue or fragment of the present invention, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act as a PDE enzyme in accordance with present invention. Amino acid substitutions may include the use of non-naturally occurring analogues, for example to increase blood plasma half-life.

The amino acid sequence of the present invention may be produced by expression of a nucleotide sequence coding for same in a suitable expression system.

In addition, or in the alternative, the protein itself could be produced using chemical methods to synthesize a PDE amino acid sequence, in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure).

Direct peptide synthesis can be performed using various solid-phase techniques (Roberge J Y et al (1995) Science 269: 202–204) and automated synthesis may be achieved, for example, using the ABI 43 1 A Peptide Synthesizer (Perkin Elmer) in accordance with the instructions provided by the manufacturer. Additionally, the amino acid sequence of PDE, or any part thereof, may be altered during direct synthesis and/or combined using chemical methods with a sequence-from other subunits, or any part thereof, to produce a variant polypeptide.

In another embodiment of the invention, a PDE natural, modified or recombinant sequence may be ligated to a heterologous sequence to encode a fusion protein. For example, for screening of peptide libraries for inhibitors of PDE activity, it may be useful to encode a chimeric PDE protein expressing a heterologous epitope that is recognised by a commercially available antibody. A fusion protein may also be engineered to contain a cleavage site located between a PDE sequence and the heterologous protein sequence, so that the PDE may be cleaved and purified away from the heterologous moiety.

PDE may also be expressed as a recombinant protein with one or more additional polypeptide domains added to facilitate protein purification. Such purification facilitating domains include, but are not limited to, metal chelating peptides such as histidine-tryptophan modules that allow purification on immobilised metals (Porath J (1992) Protein Expr Purif 3 -.26328 1), protein A domains that allow purification on immobilised immunoglobulin, and the domain utilised in the FLAGS extension/affinity purification system (Immunex Corp, Seattle, Wash.). The inclusion of a cleavable linker sequence such as Factor XA or enterokinase (Invitrogen, San Diego, Calif.) between the purification domain and PDE is useful to facilitate purification.

A specific amino acid sequence of PDE1B2 is shown as SEQ ID NO:1. However, the present invention encompasses amino acid sequences encoding other members from the PDE1B2 family which would include amino acid sequences having at least 60% identity (more preferably at least 75% identity) to that specific amino acid sequences.

Polypeptides of the present invention also include fragments of the presented amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5, or 10)

substitutions, deletions or insertions, including conserved substitutions. These aspects are discussed in a later section.

Nucleotide Sequence of the Present Invention

The term "nucleotide sequence" as used herein refers to an oligonucleotide sequence or polynucleotide sequence, and variants, homologues, fragments and derivatives thereof (such as portions thereof). The nucleotide sequence may be DNA or RNA which may be of genomic or synthetic or recombinant origin which may be double-stranded or single-stranded whether representing the sense or antisense strand.

Preferably, the term "nucleotide sequence" means DNA.

More preferably, the term "nucleotide sequence" means DNA prepared by use of recombinant DNA techniques (i.e. recombinant DNA).

In a preferred embodiment, the nucleotide sequence per se of the present invention does not cover the native nucleotide coding sequence according to the present invention in its natural environment when it is under the control of its native promoter which is also in its natural environment. For ease of reference, we have called this preferred embodiment the "non-native nucleotide sequence".

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "variant" also encompasses sequences that are complementary to sequences that are capable of hydridising to the nucleotide sequences presented herein.

Preferably, the term "variant" encompasses sequences that are complementary to sequences that are capable of hydridising under stringent conditions (e.g. 65° C. and 0.1×SSC {1×SSC=0.15 M NaCl, 0.015 Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 65° C. and 0.1× SSC).

Exemplary nucleic acids can alternatively be characterised as those nucleotide sequences which encode a PDE1B2 protein and hybridise to the DNA sequence shown in the attached sequence listings. Preferred are such sequences encoding PDE1B2 which hybridise under high-stringency conditions to the sequence shown in the attached sequence listings or the complement thereof.

Advantageously, the invention provides nucleic acid sequences which are capable of hybridising, under stringent conditions, to a fragment of the sequence shown in the attached sequence listings or the complement thereof. Preferably, the fragment is between 15 and 50 bases in length. Advantageously, it is about 25 bases in length.

The terms "variant", "homologue" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for an enzyme having PDE1B2 activity, preferably being at least as biologically active as the enzyme encoded by the sequences shown in the attached sequence listings. In particular, the term "homologue" covers homology with respect to structure and/or function providing the resultant nucleotide sequence codes for or is capable of coding for an enzyme having PDE1B2 activity. With respect to sequence homology, preferably there is at least 75%, more preferably at least 85%, more preferably at least 90% homology to a nucleotide sequence coding for the amino acid sequence shown as SEQ ID NO:1. More preferably there is at least 95%, more preferably at least 98% homology to a nucleotide sequence coding for the amino acid sequence shown as SEQ ID NO:1. Preferably, with respect to sequence homology, preferably there is at least 75%, more preferably at least 85%, more preferably at least 90% homology to the sequence shown as SEQ ID NO:2. More preferably there is at least 95%, more preferably at least 98%, homology to the sequence shown as SEQ ID NO:2.

Preferably, the variant, homologue or fragment of the present invention comprises a nucleotide sequence that encodes for at least 5 contiguous amino acids, preferably at least 10 contiguous amino acids, preferably at least 15 contiguous amino acids, preferably at least 20 contiguous amino acids, preferably at least 21 contiguous amino acids, preferably at least 22 contiguous amino acids, preferably at least 23 contiguous amino acids, preferably at least 24 contiguous amino acids, of the following N terminal sequence:

MANPVPVQRSHLQGPILRLRYMVK (SEQ ID NO:5)

As indicated, the present invention relates to a DNA sequence (preferably a cDNA sequence) encoding PDE1B2. In particular, the present invention relates to cDNA sequences encoding PDE1B2.

The present invention also relates to DNA segments comprising the DNA sequence of the sequences shown in the attached sequence listings or allelic variations of such sequences.

The present invention also relates to polypeptides produced by expression in a host cell into which has been incorporated the foregoing DNA sequences or allelic variations thereof.

The present invention also relates provides DNA comprising the DNA sequence shown in the attached sequence listings or an allelic variation thereof.

The present invention also relates to non-native DNA comprising the DNA sequence shown in the attached sequence listings or an allelic variation thereof.

A highly preferred aspect of the present invention relates to recombinant DNA comprising the DNA sequence shown in the attached sequence listings or an allelic variation thereof.

Polynucleotides of the present invention include nucleotide acid sequences encoding the polypeptides of the present invention. It will appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate PCR which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism is whose nucleic acid is used as the template DNA for the PCR procedure. PCR will be used at stringency conditions lower than those used for cloning sequences with single sequence (non-degenerate) primers against known sequences.

Nucleic acid sequences obtained by PCR that encode polypeptide fragments of the present invention may then be used to obtain larger sequences using hybridisation library screening techniques. For example a PCR clone may be labelled with radioactive atoms and used to screen a cDNA or genomic library from other species, preferably other mammalian species. Hybridisation conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other mammalian species. However, it is preferred to carry out PCR techniques initially to obtain a single sequence for use in further screening procedures.

In accordance with the present invention, PDE1B2 polynucleotide sequences which encode PDE1B2, fragments of the polypeptide, fusion proteins or functional equivalents thereof, may be used to generate recombinant DNA molecules that direct the expression of PDE1B2 in appropriate host cells. Due to the inherent degeneracy of the genetic code, other DNA sequences which encode substantially the same or a functionally equivalent amino acid sequence, may be used to clone and express PDE1B2. As will be understood by those of skill in the art, it may be advantageous to produce PDE-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PDE1B2 expression or to produce recombinant RNA transcripts having desirable properties, such as a longer half-life, than transcripts produced from naturally occurring sequence.

Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Altered PDE1B2 polynucleotide sequences which may be used in accordance with the invention include deletions, insertions or substitutions of different nucleotide residues resulting in a polynucleotide that encodes the same or a functionally equivalent PDE. The protein may also have deletions, insertions or substitutions of amino acid residues which produce a silent change and result in a functionally equivalent PDE. Deliberate amino acid substitutions may be made on the basis of similarity in polarity, charge, solubility, hydrophobicity, hydrophilicity, and/or the amphipathic nature of the residues as long as the biological activity of PDE is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Included within the scope of the present invention are alleles of PDE. As used herein, an "allele" or "allelic sequence" is an alternative form of PDE. Alleles result from a mutation, i.e., a change in the nucleic acid sequence, and generally produce altered mRNAs or polypeptides whose structure or function may or may not be altered. Any given gene may have none, one or-many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a PDE coding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns or to change codon preference.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}P$ or $^{35}S$, enzyme labels, or other protein labels such as biotin. Such labels may be added to polynucleotides or primers of the present invention and may be detected using by techniques known per se.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–30 nucleotides) to a region of the nucleotide sequence which it is desired to clone, bringing the primers into contact with mRNA or cDNA obtained from a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

DNA molecules may be modified to increase intracellular stability and half-life. Possible modifications include, but are not limited to, the addition of flanking sequences of the 5' and/or 3' ends of the molecule or the use of phosphorothioate or 2'O-methyl rather than phosphodiesterase linkages within the backbone of the molecule.

As mentioned earlier, the present invention also relates to nucleotide sequences that are capable of hybridising to all or-part of the sequence shown in the attached sequence listings or an allelic variation thereof. These nucleotide sequences may be used in anti-sense techniques to modify PDE1B2 expression. Alternatively, these sequences (or portions thereof) can be used as a probe, or for amplifying all or part of such sequence when used as a polymerase chain reaction primer.

In addition to the recombinant DNA sequences, genomic sequences are also of utility in the context of drug discovery. It may be valuable to inhibit the mRNA transcription of a particular isoform rather than to inhibit its translated protein. This may be true with PDE1B2 if there are splice variants and wherein those different splice variants may be transcribed from different promoters. There is precedent for multiple promoters directing the transcription of a mouse brain 2',3'-cyclic-nucleotide 3' phosphodiesterase (Kurihara T et al., Biochem. Biophys. Res. Comm. 170:1074 [1990]).

Another utility of the invention is that the DNA sequences, once known, give the information needed to design assays to specifically detect isoenzymes or splice variants. Isozyme-specific PCR primer pairs are but one example of an assay that depends completely on the knowledge of the specific DNA sequence of-the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific PDE1B2 isozymes are shown to associated with a particular disease state, the invention would be valuable in the design of diagnostic assays to detect the presence of isozyme mRNA.

An abnormal level of nucleotide sequences encoding a PDE1B2 in a biological sample may reflect a chromosomal aberration, such as a nucleic acid deletion or mutation. Accordingly, nucleotide sequences encoding a PDE1B2 provide the basis for probes which can be used diagnostically to detect chromosomal aberrations such as deletions, mutations or chromosomal translocations in the gene encoding PDE. PDE1B2 gene expression may be altered in such disease states or there may be a chromosomal aberration present in the region of-the gene encoding a PDE1B2.

In an alternative embodiment of the invention, the coding sequence of PDE could be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

Naturally Occurring

As used herein "naturally occurring" refers to a PDE1B2 with an amino acid sequence found in nature.

Isolated/Purified

As used herein, the terms "isolated" and "purified" refer to molecules, either nucleic or amino acid sequences, that are removed from their natural environment and isolated or separated from at least one other component with which they are naturally associated.

Biologically Active

As used herein "biologically active" refers to a PDE1B2 according to the present invention—such as a recombinant PDE1B2—having a similar structural function (but not necessarily to the same degree), and/or similar regulatory function (but not necessarily to the same degree), and/or similar biochemical function (but not necessarily to the same degree) and/or immunological activity (but not necessarily to the same degree) of the naturally occurring PDE1B2. Specifically, a PDE1B2 of the present invention has the ability to hydrolyse a cyclic nucleotide, which is one of the characteristic activities of the PDE enzyme of the present invention.

Immunological Activity

As used herein, "immunological activity" is defined as the capability of the natural, recombinant or synthetic PDE1B2 or any oligopeptide thereof, to induce a specific immune response in appropriate animals or cells and to bind with specific antibodies.

Derivative

The term "derivative" as used herein in relation to the amino acid sequence includes chemical modification of a PDE1B2. Illustrative of such modifications would be replacement of hydrogen by an alkyl, acyl, or amino group.

Deletion

As used herein a "deletion" is defined as a change in either nucleotide or amino acid sequence in which one or more nucleotides or amino acid residues, respectively, are absent.

Insertion/Addition

As used herein an "insertion" or "addition" is a change in a nucleotide or amino acid sequence which has resulted in the addition of one or more nucleotides or amino acid residues, respectively, as compared to the naturally occurring PDE.

Substitution

As used herein "substitution" results from the replacement of one or more nucleotides or amino acids by different nucleotides or amino acids, respectively.

Homologue

The term "homologue" with respect to the nucleotide sequence of the present invention and the amino acid sequence of the present invention may be synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence, has at least 75% identity to the sequence(s). Relative sequence homology (i.e. sequence identity) can also be determined by commercially available computer programs that can calculate % homology between two or more sequences. A typical example of such a computer program is CLUSTAL.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for off-line and on-line searching (see Ausubel et al., 1999 ibid, pages 7-58 to 7-60). However, for some applications it is preferred to use the GCG Bestfit program.

Although the final % homology can be measured in terms of identity, in some cases, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software-typically does this as part of the sequence comparison and generates a numerical result.

As indicated, for some applications, sequence homology (or identity) may be determined using any suitable homology algorithm, using for example default parameters. For a discussion of basic issues in similarity searching of sequence databases, see Altschul et al (1994) Nature Genetics 6:119–129. For some applications, the BLAST algorithm is employed, with parameters set to default values. The BLAST algorithm is described in detail at the NCBI web page. Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

Should Gap Penalties be used when determining sequence identity, then preferably the following parameters are used:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 10 | 10 | |
| GAP EXTENSION | 0.1 | 0.1 | |

Other computer program methods to determine identify and similarity between the two sequences include but are not limited to the GCG program package (Devereux et al 1984 Nucleic Acids Research 12: 387 and FASTA (Atschul et al 1990 J Molec Biol 403–410).

Polypeptide Variants and Derivatives

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has PDE activity, preferably having at least the same activity as the polypeptide presented in the sequence listings.

The sequences of the present invention may be modified for use in the present invention. Typically, modifications are made that maintain the PDE activity of the sequence. Amino acid substitutions may be made, for example from 1, 2 or 3 to 10, 20 or 30 substitutions provided that the modified sequence retains the PDE activity. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
| | | I L V |
| | Polar - uncharged | C S T M |
| | | N Q |
| | Polar - charged | D E |
| | | K R |
| AROMATIC | | H F W Y |

As indicated above, proteins of the invention are typically made by recombinant means, for example as described herein, and/or by using synthetic means using techniques well known to skilled persons such as solid phase synthesis. Variants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

Polynucleotide Variants and Derivatives

The terms "variant" or "derivative" in relation to the nucleotide sequence of the present invention include any substitution of, variation of, modification of, replacement of, deletion of or addition of one (or more) nucleic acid from or to the sequence providing the resultant nucleotide sequence codes for a polypeptide having PDE activity, preferably having at least the same activity as sequences presented in the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. For some applications, a preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

As used herein, the terms "variant", "homologue", "fragment" and "derivative" embrace allelic variations of the sequences.

The term "variant" also encompasses sequences that are complementary to sequences that are capable of hydridising to the nucleotide sequences presented herein.

Hybridisation

The term "hybridisation" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68° C.

Maximum stringency typically occurs at about Tm-5° C. (5° C. below the Tm of the probe).

High stringency at about 5° C. to 10° C. below the Tm of the probe. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate, or intermediate, stringency typically occurs at about 10° C. to 20° C. below the Tm of the probe.

Low stringency typically occurs at about 20° C. to 25° C. below the Tm of the probe.

As will be understood by those of skill in the art, a maximum stringency hybridisation can be used to identify or detect identical polynucleotide sequences while an intermediate (or low) stringency hybridisation can be used to identify or detect similar or related polynucleotide sequences.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Polynucleotides of the invention capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

In a preferred aspect, the present invention covers nucleotide sequences that can hybridise to any one or more of the nucleotide sequences of the present invention under stringent conditions (e.g. 65° C. and 0.1×SSC {1×SSC=0.15 M NaCl, 0.015 M Na$_3$ Citrate pH 7.0).

Where the polynucleotide of the present invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the sequence in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Regulatory Sequences

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

Secretion

Often, it is desirable for the polypeptide of the present invention to be secreted from the expression host into the culture medium from where the polypeptide of the present invention may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces* and *Kluyveromyces*) or the α-amylase gene (*Bacillus*).

Constructs

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention.

The same is true for the term "fused" in relation to the present invention which includes direct or indirect attachment. In each case, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

Preferably the construct of the present invention comprises at least the nucleotide sequence of the present invention operably linked to a promoter.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *E.coli* plasmid to a bacterium, such as of the genus *Bacillus*, then the transformation vector is sometimes called a "shuttle vector". It may even be a construct capable of being transferred from an *E.coli* plasmid to an *Agrobacterium* to a plant.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pyrA), phleomycin and benomyl resistance (benA).

Examples of non-fungal selection markers are the bacterial G418 resistance gene (this may also be used in yeast, but not in filamentous fungi), the ampicillin resistance gene (*E. coli*), the neomycin resistance gene (*Bacillus*) and the *E.coli* uidA gene, coding for β-glucuronidase (GUS).

Vectors may be used in vitro, for example for the, production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

The present invention also relates to the use of genetically engineered host cells expressing a PDE1B2 or variant, homologue, fragment or derivative thereof in screening methods for the identification of inhibitors and antagonists of the PDE1B2 that would modulate phosphodiesterase activity thereby modulating cyclic nucleotide levels. Such genetically engineered host cells could be used to screen peptide libraries or organic molecules capable of modulating PDE1B2 activity. Antagonists and inhibitors of PDE1B2 such as antibodies, peptides or small organic molecules will provide the basis for pharmaceutical compositions for the treatment of diseases associated with, for example, PDE1B2. Such inhibitors or antagonists can be administered alone or in combination with other therapeutics for the treatment of such diseases.

The present invention also relates to expression vectors and host cells comprising polynucleotide sequences encoding PDE1B2 or variant, homologue, fragment or derivative thereof for the in vivo or in vitro production of PDE1B2 protein or to screen for agents that can affect PDE1B2 expression or activity.

Tissue

The term "tissue" as used herein includes tissue per se and organ.

Host Cells

The term "host cell"—in relation to the present invention includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotides. The cells will be chosen to be compatible with the said vector and may for example be prokaryotic (for example bacterial), fungal, yeast or plant cells.

The gram-negative bacterium *E. coli* is widely used as a host for heterologous gene expression. However, large amounts of heterologous protein tend to accumulate inside the cell. Subsequent purification of the desired protein from the bulk of *E.coli* intracellular proteins can sometimes be difficult.

In contrast to *E.coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the recombinant protein according to the present invention and/or products obtained therefrom, wherein a promoter can allow expression of the nucleotide sequence according to the present invention when present in the organism. Examples of organisms may include a fungus, yeast or a plant.

The term "transgenic organism" in relation to the present invention includes any organism that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment. In addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

Transformation of the Host Cells/Host Organisms

As indicated earlier, the host organism can be a prokaryotic or a eukaryotic organism. Examples of suitable prokaryotic hosts include E. coli and Bacillus subtilis. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons Saccharomyces cerevisiae is well suited for heterologous gene expression. First, it is, non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of Saccharomyces cerevisiae.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques,may be found in articles by Potrykus (Annu Rev Plant Physiol Plant Mol Biol [1991 ] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence shown in the attached sequence listings or a derivative, homologue, variant or fragment thereof.

Host cells transformed with a PDE nucleotide coding sequence may be cultured under conditions suitable for the expression and recovery of the encoded protein from cell culture. The protein produced by a recombinant cell may be secreted or may be contained intracellularly depending on the sequence, and/or the vector used. As will be understood by those of skill in the art, expression vectors containing PDE coding sequences can be designed with signal sequences which direct secretion of PDE coding sequences through a particular prokaryotic or eukaryotic cell membrane. Other recombinant constructions may join PDE coding sequence to nucleotide sequence encoding a polypeptide domain which will facilitate purification of soluble. proteins (Kroll D J et al (1993) DNA Cell Biol 12:441–53, see also above discussion of vectors containing fusion proteins).

Production of the Polypeptide

According to the present invention, the production of the polypeptide of the present invention can be effected by the culturing of, for example, microbial expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating micro-organisms.

Thus, the present invention also provides a method for producing a polypeptide having PDE1B2 activity, the method comprising the steps of a) transforming a host cell with a nucleotide sequence shown in the attached sequence listings or a derivative, homologue, variant or fragment thereof; and b) culturing the transformed host cell under conditions suitable for the expression of said polypeptide.

The present invention also provides a method for producing a polypeptide having PDE1B2 activity, the method comprising the steps of a) culturing a host cell that has been transformed with a nucleotide sequence shown in the attached sequence listings or a derivative, homologue, variant or fragment thereof under conditions suitable for the expression of said polypeptide; and b) recovering said polypeptide from the host cell culture.

The present invention also provides a method for producing a polypeptide having PDE1B2 activity, the method comprising the steps of a) transforming a host cell with a nucleotide sequence shown in the attached sequence listings or a derivative, homologue, variant or fragment thereof; b) culturing the transformed host cell under conditions suitable for the expression of said polypeptide; and c) recovering said polypeptide from the host cell culture.

Ribozymes

Ribozymes are enzymatic RNA molecules capable of catalysing the specific cleavage of RNA. The mechanism of ribozyme action involves sequence specific hybridisation of the ribozyme molecule to complementary target RNA, followed by a endonucleolytic cleavage. Within the scope of the invention are engineered hammerhead motif ribozyme molecules that specifically and efficiently catalyse endonucleolytic cleavage of PDE RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may- also be evaluated by testing accessibility to hybridisation with complementary oligonucleotides using ribonuclease protection assays.

Both antisense RNA and DNA molecules and ribozymnes of the invention may be prepared by any method known in the art for the synthesis of RNA molecules. These include techniques for chemically synthesising oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

Detection

The presence of the PDE polynucleotide coding sequence can be detected by DNA-DNA or DNA-RNA hybridisation or amplification using probes, portions or fragments of the sequence presented in the attached sequence listings. Nucleic acid amplification based assays involve the use of oligonucleotides or oligomers based on the PDE coding sequence to detect transformants containing PDE DNA or RNA. As used herein "oligonucleotides" or "oligomers" may refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the nucleotide sequence shown in the attached sequence listings.

A variety of protocols for detecting and measuring the expression of PDE polypeptide, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on PDE polypeptides is preferred, but a competitive binding assay may be employed. These and other assays are described, among other places, in Hampton R et al (1990, Serological Methods, A Laboratory Manual, APS Press, St Paul Minn.) and Maddox D E et al (1983, J Exp Med 15 8:121 1).

A wide variety of labels and conjugation techniques are known by those skilled in the art and can be used in various nucleic and amino acid assays. Means for producing labelled hybridisation or PCR probes for detecting PDE polynucleotide sequences include oligolabelling, nick translation, end-labelling or PbR amplification using a labelled nucleotide. Alternatively, the PDE coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,276,149 and 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the PDE coding sequence is inserted within a marker gene sequence, recombinant cells containing PDE coding regions can be identified by the absence of marker gene function. Alternatively, a marker gene can be placed in tandem with a PDE coding sequence under the control of a single promoter. Expression of the marker gene in response to induction or selection usually indicates expression of PDE as well.

Alternatively, host cells which contain the coding sequence for PDE and express PDE coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

Antibodies

The amino acid sequence of the present invention can also be used to generate antibodies—such as by use of standard techniques—against the amino acid sequence.

Procedures well known in the art may be used for the production of antibodies to PDE1B2 polypeptides. Such antibodies include, but are not limited to, polyclonal, monoclonal, chimeric, single chain, Fab fragments and fragments produced by a Fab expression library. Neutralising antibodies, i.e., those which inhibit biological activity of PDE polypeptides, are especially preferred for diagnostics and therapeutics.

For the production of antibodies, various hosts including goats, rabbits, rats, mice, etc. may be immunised by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed.

Monoclonal antibodies to the amino acid sequence may be even prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PDE1B2 may also be generated. For example, such fragments include, but are not limited to, the F(ab')$_2$ fragments which can be produced by pepsin digestion of the antibody molecule and the Fab fragments which can be generated by reducing the disulphide bridges of the F(ab')$_2$ fragments. Alternatively, Fab expression libraries may be constructed to allow rapid and easy identification of monoclonal Fab fragments with the desired specificity (Huse W D et al (1989) Science 256:1275–128 1).

An alternative technique involves screening phage display libraries where, for example the phage express scFv fragments on the surface of their coat with a large variety of complementarity determining regions (CDRs). This technique is well known in the art.

PDE1B2-specific antibodies are useful for the diagnosis of conditions and diseases associated with expression of PDE1B2 polypeptide. A variety of protocols for competitive binding or immunoradiometric assays using either polyclonal or monoclonal antibodies with established specificities are well known in the art. Such immunoassays typically involve the formation of complexes between PDE1B2 polypeptides and its specific antibody (or similar PDE1B2-binding molecule) and the measurement of complex formation. A two-site, monoclonal based immunoassay utilising monoclonal antibodies reactive to two non-interfering epitopes on a specific PDE1B2 protein is preferred, but a competitive binding assay may also be employed. These assays are described in Maddox D E et al (1983, J Exp Med 158:121 1).

Anti-PDE1B2 antibodies are useful for the diagnosis of inflammation, conditions associated with proliferation of haematopoietic cells and HIV infection or other disorders or diseases characterised by abnormal expression of a PDE1B2. Diagnostic assays for a PDE1B2 include methods utilising the antibody and a label to detect a PDE1B2 polypeptide in human body fluids, cells, tissues or sections or extracts of such tissues.

The polypeptides and antibodies of the present invention may be used with or without modification. Frequently, the polypeptides and antibodies will be labelled by joining them, either covalently or noncovalently, with a reporter molecule. A wide variety of reporter molecules are known to those of skill in the art.

Antibodies may be used in method of detecting polypeptides of the invention present in biological samples by a method which comprises: (a) providing an antibody of the invention; (b) incubating a biological sample with said antibody under conditions which allow for the formation of an antibody-antigen complex; and (c) determining whether antibody-antigen complex comprising said antibody is formed.

Depending on the circumstances, suitable samples may include extracts tissues such as brain, breast, ovary, lung, colon, pancreas, testes, liver, muscle and bone tissues or from neoplastic growths derived from such tissues.

Antibodies of the invention may be bound to a solid support and/or packaged into kits in a suitable container along with suitable reagents, controls, instructions and the like.

Assays/Identification Methods

The present invention also relates to an assay method for detecting the presence of PDE1B2 in cells (such as human cells) comprising: (a) performing a reverse transcriptase-polymerase chain reaction on RNA (such as total RNA) from such cells using a pair of polymerase chain reaction primers that are specific for PDE1B2, as determined from the DNA sequence shown in the attached sequence listings or an allelic variation thereof; and (b) assaying the appearance of an appropriately sized PCR (polymerase chain reaction) fragment—such as by agarose gel electrophoresis.

The present invention also relates to a method of identifying agents (such as compounds, other substances or compositions comprising same) that affect (such as inhibit or otherwise modify) the activity of PDE1B2 and/or the expression thereof, the method comprising contacting PDE1B2 or the nucleotide sequence coding for same with the agent and then measuring the activity of PDE1B2 and/or the expression thereof.

The present invention also relates to a method of identifying agents (such as compounds, other substances or compositions comprising same) that selectively affect (such as inhibit or otherwise modify) the activity of PDE1B2 and/or the expression thereof, the method comprising contacting PDE1B2 or the nucleotide sequence coding for same with the agent and then measuring the activity of PDE1B2 and/or the expression thereof.

The present invention also relates to a method of identifying agents (such as compounds, other substances or compositions comprising same) that affect (such as inhibit or otherwise modify) the activity of PDE1B2 and/or the expression thereof, the method comprising measuring the activity of PDE1B2 and/or the expression thereof in the presence of the agent or after the addition of the agent in: (a) a cell, line into which has been incorporated recombinant DNA comprising the DNA sequence shown in the attached sequence listings or an allelic variation thereof, or (b) a cell population or cell line that naturally selectively expresses PDE1B2. Preferably, the activity of PDE1B2 is determined by the assay method described above.

The present invention also relates to a method of identifying agents (such as compounds, other substances or compositions comprising same) that selectively affect (such as inhibit or otherwise modify) the activity of PDE1B2 and/or the expression thereof, the method comprising measuring the activity of PDE1B2 and/or the expression thereof in the presence of the agent or after the addition of the agent in: (a) a cell line into which has been incorporated recombinant DNA comprising the DNA sequence shown in the attached sequence listings or an allelic variation thereof, or (b) a cell population or cell line that naturally selectively expresses PDE1B2. Preferably, the activity of PDE1B2 is determined by the assay method described above.

The present invention also provides a method of screening an agent for modulation (preferably for specific modulation) of PDE1B2 (or a derivative, homologue, variant or fragment thereof) activity or the expression of the nucleotide sequence coding for same (including a derivative, homologue, variant or fragment thereof), the method comprising the steps of: a) providing a candidate agent; b) combining PDE1B2 (or the derivative, homologue, variant or fragment thereof) or the nucleotide sequence coding for same (or the derivative, homologue, variant or fragment thereof) with the candidate agent for a time sufficient to allow modulation under suitable conditions; and c) detecting modulation of the candidate agent to PDE1B2 (or the derivative, homologue, variant or fragment thereof) or the nucleotide sequence coding for same (or the derivative, homologue, variant or fragment thereof) in order to ascertain if the candidate agent modulates PDE1B2 (or the derivative, homologue, variant or fragment thereof) activity or the expression of the nucleotide sequence coding for same (or the derivative, homologue, variant or fragment thereof).

The present invention also provides a method of screening an agent for specific binding affinity with PDE1B2 (or a derivative, homologue, variant or fragment thereof) or the nucleotide sequence coding for same (including a derivative, homologue, variant or fragment thereof), the method comprising the steps of: a) providing a candidate agent; b) combining PDE1B2 (or the derivative, homologue, variant or fragment thereof) or the nucleotide sequence coding for same (or the derivative, homologue, variant or fragment thereof) with the candidate agent for a time sufficient to allow binding under suitable conditions; and c) detecting binding of the candidate agent to PDE1B2 (or the derivative, homologue, variant or fragment thereof) or the nucleotide sequence coding for same (or the derivative, homologue, variant or fragment thereof) in order to ascertain if the candidate agent binds tot PDE1B2 (or the derivative, homologue, variant or fragment thereof) or the nucleotide sequence coding for same (or the derivative, homologue, variant or fragment thereof).

The present invention also provides a method of identifying an agent which is capable of modulating PDE1B2, the method comprising the steps of: a) contacting the agent with PDE1B2 (or a derivative, homologue, variant or fragment thereof) or the nucleotide sequence coding for same (or the derivative, homologue, variant or fragment thereof), b) incubating the mixture of step a) with a cyclic nucleotide under conditions suitable for the hydrolysis of the cyclic nucleotide, c) measuring the amount of cyclic nucleotide hydrolysis, and d) comparing the amount of cyclic nucleotide hydrolysis of step c) with the amount of cyclic nucleotide hydrolysis obtained with PDE1B2 (or the derivative, homologue, variant or fragment thereof) or the nucleotide sequence coding for same (or the derivative, homologue, variant or fragment thereof) incubated without the compound, thereby determining whether the agent affects (such as stimulates or inhibits) cyclic nucleotide hydrolysis.

Thus, in certain embodiments of the present invention, PDE1B2 or a variant, homologue, fragment or derivative thereof and/or a cell line that expresses the PDE1B2 or variant, homologue, fragment or derivative thereof may be used to screen for antibodies, peptides, or other agent, such as organic or inorganic molecules, that act as modulators of phosphodiesterase activity or for the expression thereof, thereby identifying a therapeutic agent capable of modulating cyclic nucleotide levels. For example, anti-PDE1B2 antibodies capable of neutralising the activity of PDE1B2 may be used to inhibit PDE1B2 hydrolysis of cyclic nucleotides, thereby increasing their levels. Alternatively, screening of peptide libraries or organic libraries made by combinatorial chemistry with recombinantly expressed PDE1B2 or a variant, homologue, fragment or derivative thereof or cell lines expressing PDE1B2 or a variant, homologue, fragment or derivative thereof may be useful for identification of therapeutic agents that function by modulating PDE1B2 hydrolysis of cyclic nucleotides. Synthetic compounds, natural products, and other sources of potentially biologically active materials can be screened in a number of ways deemed to be routine to those of skill in the art. For example, nucleotide sequences encoding the N-terminal region of PDE1B2 may be expressed in a cell line which can be used for screening of allosteric modulators, either, agonists or antagonists, of PDE1B2 activity. Alternatively, nucleotide sequences encoding the conserved catalytic domain of PDE1B2 can be expressed in cell lines and used to screen for inhibitors of cyclic nucleotide hydrolysis.

The ability of a test agent to interfere with PDE1B2 activity or cyclic nucleotide hydrolysis may be determined by measuring PDE1B2 levels or cyclic nucleotide levels (as disclosed in Smith et al 1993 Appl. Biochem. Biotechnol. 41:189–218). There are also commercially available immunoassay kits for the measurement of cAMP and cGMP (eg Amersham International, Arlington Heights, Ill. and DuPont, Boston, Mass.). The activity of PDE1B2 may also be monitored by measuring other responses such as phosphorylation or dephosphorylation of other proteins using conventional techniques developed for these purpose.

Accordingly, the present invention provides a method of identifying a compound which is capable of modulating the cyclic nucleotide phosphodiesterase activity of a PDE1B2, or a variant, homologue, fragment or derivative thereof, comprising the steps of a) contacting the compound with a PDE1B2, or a variant, homologue, fragment or derivative thereof; b) incubating the mixture of step a) with a cyclic nucleotide under conditions suitable for the hydrolysis of the cyclic nucleotide; c) measuring the amount of cyclic nucleotide hydrolysis; and d) comparing the amount of cyclic nucleotide hydrolysis of step c) with the amount of cyclic nucleotide hydrolysis obtained with the PDE1B2, or a variant, homologue, fragment or derivative thereof, incubated without the compound, thereby determining whether the compound stimulates or inhibits cyclic nucleotide hydrolysis. In one embodiment of the method, the fragment may be from the N-terminal region of the PDE1B2 and provides a method to identify allosteric modulators of the PDE1B2. In another embodiment of the present invention, the fragment may be from the carboxy terminal region of the PDE1B2 and provides a method to identify inhibitors of cyclic nucleotide hydrolysis.

A PDE1B2 polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The abolition of activity or the formation of binding complexes between a PDE1B2 polypeptide and the agent being tested may be measured.

Accordingly, the present invention provides a method for screening one or a plurality of compounds for modulation (preferably specific modulation, such as specific binding affinity) of PDE1B2 or the expression thereof, or a portion thereof or variant, homologue, fragment or derivative thereof, comprising providing one or a plurality of compounds; combining a PDE1B2 or a nucleotide sequence coding for same or a portion thereof or variant, homologue, fragment or derivative thereof with the or each of a plurality of compounds for a time sufficient to allow modulation under suitable conditions; and detecting binding of a PDE1B2, or portion thereof or variant, homologue, fragment or derivative thereof, to each of the plurality of compounds, thereby identifying the compound or compounds which modulate a PDE1B2 or a nucleotide sequence coding for same. In such an assay, the plurality of compounds may be produced by combinatorial chemistry techniques known to those of skill in the art.

Another technique for drug screening provides for high throughput screening of compounds having suitable binding affinity to the PDE1B2 polypeptides and is based upon the method described in detail in Geysen, European Patent Application 84/03564, published on Sep. 13, 1984. In summary, large numbers of different small peptide test compounds are synthesized on a solid substrate, such as plastic pins or some other surface. The peptide test compounds are reacted with PDE1B2 fragments and washed. A bound PDE1B2 is then detected—such as by appropriately adapting methods well known in the art. A purified PDE1B2 can also be coated directly onto plates for use in the aforementioned drug screening techniques. Alternatively, non-neutralising antibodies can be used to capture the peptide and immobilise it on a solid support.

This invention also contemplates the use of competitive drug screening assays in which neutralising antibodies capable of binding a PDE1B2 specifically compete with a test compound for binding a PDE1B2. In this manner, the antibodies can be used to detect the presence of any peptide which shares one or more antigenic determinants with a PDE1B2.

The assay method of the present invention may be a high throughput screen (HTS). In this regard, the teachings of WO 84/03564 may be adapted for the PDE of the present invention.

The teachings of U.S. Pat. No. 5,738,985 may be adapted for the assay method of the present invention.

Agents

The present invention also provides one or more agents identified by the assays methods and identification methods of the present invention.

The agent, of the present invention can be, for example, an organic compound or an inorganic compound. The agent can be, for example, a nucleotide sequence that is anti-sense to all or part of the sequences shown in the attached sequence listings.

The invention further provides an agent of the present invention (or even a pharmaceutically acceptable salt thereof, or a pharmaceutically acceptable solvate thereof) or a pharmaceutical composition containing any of the foregoing, for use as a medicament.

The present invention also provides the use of an agent to affect PDE1B2 activity (such as to inhibit, modulate or agonise) in any one or more of the cardiovascular system, the GI system, spleen.

Diagnostics

The present invention also provides a diagnostic composition for the detection of PDE1B2 polynucleotide sequences. The diagnostic composition may comprise any one of the sequences shown in the attached sequence listings or a variant, homologue, fragment or derivative thereof, or a sequence capable of hybridising to all or part of any one of the nucleotide sequence shown in the attached sequence listings or an allelic variation thereof.

In order to provide a basis for the diagnosis of disease, normal or standard values from a PDE1B2 polypeptide expression should be established. This is accomplished by combining body fluids or cell extracts taken from normal subjects, either animal or human, with antibody to a PDE1B2 polypeptide under conditions suitable for complex formation which are well known in the art. The amount of standard complex formation may be quantified by comparing it to a dilution series of positive controls where a known amount of antibody is combined with, known concentrations of a purified PDE1B2 polypeptide. Then, standard values obtained from normal samples may be compared with values obtained from samples from subjects potentially affected by a disorder or disease related to a PDE1B2 polypeptide expression. Deviation between standard and subject values establishes the presence of the disease state.

A PDE1B2 polynucleotide, or any part thereof, may provide the basis for a diagnostic and/or a therapeutic compound. For diagnostic purposes, PDE1B2 polynucleotide sequences may be used to detect and quantify gene expression in conditions, disorders or diseases in which PDE1B2 activity may be implicated.

PDE1B2 encoding polynucleotide sequence may be used for the diagnosis of diseases resulting from expression of PDE1B2. For example, polynucleotide sequences encoding PDE1B2 may be used in hybridisation or PCR assays of tissues from biopsies or autopsies or biological fluids, such as serum, synovial fluid or tumour biopsy, to detect abnormalities in PDE1B2 expression. The form of such qualitative or quantitative methods may include Southern or northern analysis, dot blot or other membrane-based technologies; PCR technologies; dip stick, pin or chip technologies; and ELISA or other multiple sample formal technologies. All of these techniques are well known in the art and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for PDE expression should be established. This is accomplished by combining body fluids or cell extracts taken from normal subjects, either animal or human, with PDE1B2 or a portion thereof, under conditions suitable for hybridisation or amplification. Standard hybridisation may be quantified by comparing the values obtained for normal subjects with a dilution series of positive controls run in the same experiment where a known amount of purified PDE1B2 is used. Standard values obtained from normal samples may be compared with values obtained from samples from subjects potentially affected by a disorder or disease related to expression of the PDE coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, the present invention relates to the use of a PDE1B2 polypeptide, or variant, homologue, fragment or derivative thereof, to produce anti-PDE1B2 antibodies which can, for example, be used diagnostically to detect and quantify PDE1B2 levels in disease states.

The present invention further provides diagnostic assays and kits for the detection of PDE1B2 in cells and tissues comprising a purified PDE1B2 which may be used as a positive control, and anti-PDE1B2 antibodies. Such antibodies may be used in solution-based, membrane-based, or tissue-based technologies to detect any disease state or condition related to the expression of PDE1B2 protein or expression of deletions or a variant, homologue, fragment or derivative thereof.

Probes

Another aspect of the subject invention is the provision of nucleic acid hybridisation or PCR probes which are capable of detecting polynucleotide sequences, including genomic sequences, encoding PDE coding region or closely related molecules, such as alleles. The specificity of the probe, i.e., whether it is derived from a highly conserved, conserved or non-conserved region or domain, and the stringency of the hybridisation or amplification (high, intermediate or low) will determine whether the probe identifies only naturally occurring PDE coding sequence, or related sequences. Probes for the detection of related nucleic acid sequences are selected from conserved or highly conserved nucleotide regions of cyclic nucleotide PDE family members, such as the 3' region, and such probes may be used in a pool of degenerate probes. For the detection of identical nucleic acid sequences, or where maximum specificity is desired, nucleic acid probes are selected from the non-conserved nucleotide regions or unique regions of PDE polynucleotides. As used herein, the term "non-conserved nucleotide region" refers to a nucleotide region that is unique to the PDE coding sequence disclosed herein and does not occur in related family members, such as known cyclic nucleotide PDEs.

PCR as described in U.S. Pat. Nos. 4,683,195, 4,800,195 and 4,965,188 provides additional uses for oligpnucleotides based upon the PDE1B2 sequence. Such oligomers are generally chemically synthesized, but they may be generated enzymatically or produced from a recombinant source. Oligomers generally comprise two nucleotide sequences, one with sense orientation (5'->3') and one with antisense (3'<-5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for PDE1B2 can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localised by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceuticals

The present invention also provides a pharmaceutical composition for treating an individual in need of same due to PDE1B2 activity, the composition comprising a therapeutically effective amount of an agent that affects (such as inhibits) said activity and a pharmaceutically acceptable carrier, diluent, excipient or adjuvant.

Thus, the present invention also covers pharmaceutical compositions comprising the agents of the present invention (an agent capable of modulating the expression pattern of the nucleotide sequence of the present invention or the activity of the expression product thereof and/or an agent identified by an assay according to the present invention). In this regard, and in particular for human therapy, even though the agents of the present invention can be administered alone, they will generally be administered in admixture with a pharmaceutical carrier, excipient or diluent selected with regard to the intended route of administration and standard pharmaceutical practice.

By way of example, in the pharmaceutical compositions of, the present invention, the agents of the present invention may be admixed with any suitable binder(s), lubricant(s), suspending agent(s), coating agent(s), or solubilising agent(s).

In general, a therapeutically effective daily oral or intravenous dose of the agents of the present invention is likely to range from 0.01 to 50 mg/kg body weight of the subject to be treated, preferably 0.1 to 20 mg/kg. The agents of the present invention may also be administered by intravenous infusion, at a dose which is likely to range from 0.001–10 mg/kg/hr.

Tablets or capsules of the agents may be administered singly or two or more at a time, as appropriate. It is also possible to administer the agents of the present invention in sustained release formulations.

Thus, the present invention also provides a method of treating an individual in need of same due to PDE1B2 activity comprising administering to said individual an effective amount of the pharmaceutical composition of the present invention.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

In some applications, generally, in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally, e.g. sublingually or buccally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatment, it may be possible to administer the agent alone for veterinary treatments.

Typically, the pharmaceutical compositions—which may be for human or animal usage—will comprise any one or more of a pharmaceutically acceptable diluent, carrier, excipient or adjuvant. The choice of pharmaceutical carrier, excipient or diluent can be selected with regard to the intended route of administration and standard pharmaceutical practice. As indicated above, the pharmaceutical compositions may comprise as—or in addition to—the carrier, excipient or diluent any suitable binder(s), lubricant(s), suspending agent(s), coating agent(s), solubilising agent(s).

In some embodiments of the present invention, the pharmaceutical compositions will comprise one or more of: an agent that has been screened by an assay of the present invention; an agent that is capable of interacting with any one of the sequences shown in the attached sequence listings including derivatives, fragments, homologues or variants, thereof or sequences capable of hybridising to the nucleotide sequence shown in the attached sequence listings.

Included in the scope of the invention are oligonucleotide sequences, antisense RNA and DNA molecules and ribozymes, which function to destabilise PDE1B2 mRNA or inhibit translation of a PDE1B2. Such nucleotide sequences may be used in conditions where it would be preferable to increase cyclic nucleotide levels, such as in inflammation.

A PDE1B2 antisense molecule may provide the basis for treatment of various abnormal conditions related to, for example, increased PDE1B2 activity.

A PDE1B2 nucleic acid antisense molecule may be used to block the activity of the PDE1B2 in conditions where it would be preferable to elevate cyclic nucleotide levels.

Expression vectors derived from retroviruses, adenovirus, herpes or vaccinia viruses, or from various bacterial plasmids, may be used for delivery of recombinant PDE1B2 sense or antisense molecules to the targeted cell population. Methods which are well known to those skilled in the art can be used to construct recombinant vectors containing PDE1B2. Alternatively, recombinant PDE1B2 can be delivered to target cells in liposomes.

The full length cDNA sequence and/or its regulatory elements enable researchers to use PDE1B2 as a tool in sense (Youssoufian H and H F Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions. Appropriate oligonucleotides, which can be 20 nucleotides in length, may be used to isolate PDE1B2 sequences or closely related molecules from human libraries.

Additionally, PDE1B2 expression can be modulated by transfecting a cell or tissue with expression vectors which express high levels of a PDE1B2 fragment in conditions where it would be preferable to block phosphodiesterase activity thereby increasing cyclic nucleotide levels. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication elements are part of the vector system.

Modifications of gene expression can be obtained by designing antisense sequences to the control regions of the PDE gene, such as the promoters, enhancers, and introns.

Oligonucleotides derived from the transcription initiation site, e.g., between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Thus the invention provides a pharmaceutical composition comprising an agent of the present invention (or even a pharmaceutically acceptable salt thereof, or a pharmaceutically acceptable solvate thereof) together with a pharmaceutically acceptable diluent, excipient or carrier.

The pharmaceutical composition could be for veterinary (i.e. animal) usage or for human usage.

Thus, the present invention therefore also relates to pharmaceutical compositions comprising effective amounts of inhibitors or antagonists of PDE1B2 protein (including anti-sense nucleic acid sequences) in admixture with a pharmaceutically acceptable diluent, carrier, excipient or adjuvant (including combinations thereof).

The present invention relates to pharmaceutical compositions which may comprise all or portions of PDE1B2 polynucleotide sequences, PDE1B2 antisense molecules, PDE1B2 polypeptides, protein, peptide or organic modulators of PDE1B2 bioactivity, such as inhibitors, antagonists (including antibodies) or agonists, alone or in combination with at least one other agent, such as stabilising compound, and may be administered in any sterile, biocompatible pharmaceutical carrier, including, but not limited to, saline, buffered saline, dextrose, and water.

General Methodology References

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4$^{th}$ Ed, John Wiley & Sons, Inc. PCR is described in U.S. Pat. Nos. 4,683,195, 4,800,195 and 4,965,188.

Deposits

The following sample was deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 9 Sept. 1999:

NCIMB number NCIMB 41026 is *Escherichia coli* (pHSPDE1B2).

The depositor was Pfizer Central Research, Pfizer Limited, Ramsgate Road, Sandwich, Kent, CT13 9NJ, United Kingdom.

The deposit was prepared as indicated in the following Examples section.

The present invention also encompasses sequences derivable and/or expressable from that deposit and embodiments comprising the same. The present invention also encompasses partial sequences derivable and/or expressable from that deposit and embodiments comprising the same, wherein those partial sequences code for active enzymatic sites. The present invention also encompasses proteins comprising sequences derivable and/or expressable from that deposit and embodiments comprising the same. The present invention also encompasses proteins comprising partial sequences derivable and/or expressable from that deposit and embodiments comprising the same, wherein those partial sequences code for active enzymatic sites.

The present invention also encompasses sequences derivable and/or expressable from that deposit and embodiments comprising the same.

Introduction to the Examples Section and the Figures

The present invention will now be described, by way of example only, with reference to the accompanying drawings in which:-

FIG. 1 presents a series of sequences;

FIG. 2 presents an image;

FIG. 3 presents some schematic diagrams;

FIG. 4 presents a series of sequences; and

Figure 5:
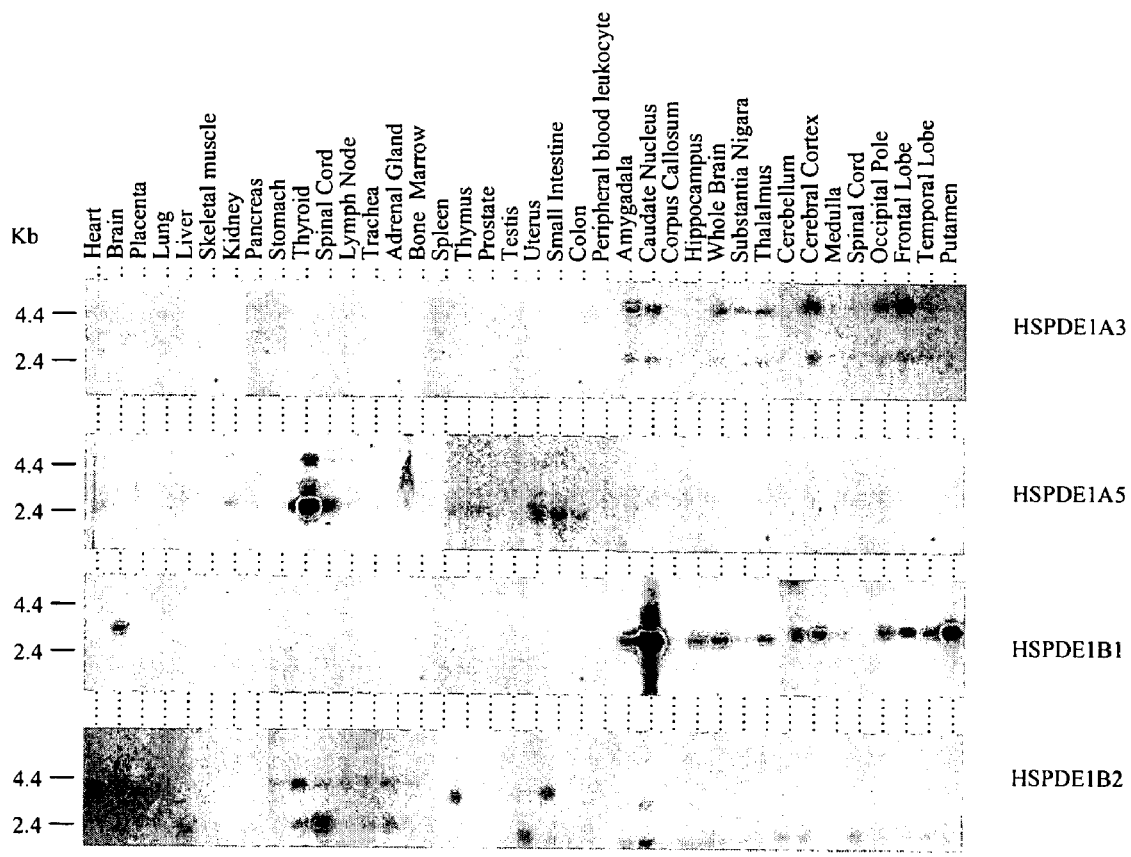
FIG. 5 presents an image of comparative Northern Blot analysis of PDE1A and PDE1B alternate splice variants with notation of the tissue source of the mRNA in the legend.

FIG. 5 presents a series of Northern blots.

In more detail:

FIG. 1.

Multiple Alignment of the PDE1 Gene Family.

Amino acid number is indicated to the left. Residues in bold identify the region used to design the degenerate capture oligonucleotide. Amino acid identity is indicated an asterix. Accession numbers for the sequences shown in this alignment are: PDE1A U40370, PDE1B U56976, PDE1C U40371.

FIG. 2.

Java Applet

This Java applet allowed the rapid alignment of DNA sequence data with the target PDE sequence and visualised those which originated from the same clone. The PDE sequence is displayed as the black bar at the top of the window, and the different clones that matched that PDE as the coloured bars beneath it. The different colours represent which library the clones came from, and their horizontal position indicates where they matched the PDE sequences. Using the menus the user can select specific libraries, or change the PDE at the sequence. By right clicking they can view alignments and get more details on each match.

FIG. 3.

Multiple Alignment of Alternative Splice Variants of PDE1A Gene.

A schematic representation of PDE1A1, PDE1A2, PDE1A3, PDE1A4 and PDE1A5 cDNAs. Divergent sequences are indicated by patterns and shading. Regions of the cDNA used for probe generation are indicated by black bars.

FIG. 4.

Alignment of N-terminal Sequences of PDE1A and PDE1B Splice Variants.

FIGS. 4A and 4B show a Clustalw alignment of the differential N-terminal regions of the PDE1A and PDE1B genes respectively. FIG. 4C, Clustalw alignment illustrating the similarity between the potential CaM binding domain of PDE1B2 and PDE1A1 suggesting that there will also be similarity in their CaM binding affinities. FIG. 4D, Clustalw alignment illustrating the homology between the CaM binding domain of PDE1A2 and PDE1B1 which has been shown to confer similar CaM binding affinities[34] In all cases the arrow indicates the point of divergence in both the PDE1A and PDE1B gene. The amino acids within the box have previously been shown to bind with CaM [34] and the asterix indicates amino acid residues that are conserved.

FIG. 5.

Comparative Northern Blot Analysis of PDE1A and PDE1B Alternative Splice Variants.

Five multiple tissue northerns (Clontech) were probed using specific PDE1A and PDE1B splice variant probes. A transcript of 4.8 kb and 2.4 kb was observed for PDE1A3 and PDE1A5 respectively. Transcripts of 3.6 kb and 2.4 kb were clearly observed for PDE1B1 and PDE1B2 respectively. Each lane contains 2 μg of poly(A) selected mRNA isolated from the tissues indicated. The position of the RNA markers are shown on the left.

EXAMPLES

Abbreviations
PDE=phosphodiesterase
kDa=kilodalton
bp=base pair
kb=kilobase pair
cAMP=adenosine 3'5'-cyclic monophosphate
cGMP=guanosine 3'5'-cyclic monophosphate
HS=*Homo sapiens*
MM=*Mus musculus*
kcaM=concentration of CaM to achieve half-maximal activation
CaM=Calmodulin Introduction Phosphodiesterases catalyse the hydrolysis of the second messenger 3', 5' cyclic nucleotides to their respective 5' monophosphates. This is an important physiological mechanism for the regulation of intracellular levels of cyclic nucleotides in response to multiple extracellular stimuli such as neurotransmitters, light and hormones. The phosphodiesterase superfamily comprises of 10 biochemically distinct families which are characterised by differences in kinetic properties, regulatory factors, inhibitor sensitivity and amino acid sequence. The 10 families contain 19 different genes, many of which encode multiple alternative splice variants expressed in a tissue specific manner [1–6]. A common feature of all PDE families is a conserved region of approximately 250 amino acids that contains the catalytic site [7–10]. Certain PDEs regulated allosterically by cGMP, calmodulin binding or phosphorylation to regions amino-terminal to the catalytic site have been described [11–13].

The PDE1 family comprises of three related genes PDE1A, 1B and 1C, which have been cloned from many different species including, bovine, human, rat & mouse [11,15,23–27]. This family is linked not only through a high degree of sequence similarity but also by a common regulatory mechanism. Activation of the PDE1's is achieved through the binding of calmodulin (CaM) in the presence of calcium, which leads to increases in the rate of cyclic nucleotide hydrolysis [11,12,14,15]. In addition, protein. phosphorylation, mediated by cAMP dependant protein kinase, (PDE1A) [16, 17],& CaM- dependant protein Kinase, (PDE1B) [18], has been demonstrated to increase the Kcam; this effectively reduces the sensitivity of each isozyme to activation by calcium [19,20]. These sensitive regulator mechanisms allow the PDE1 isozymes to play a central role in mediating signalling via is cyclic nucleotides (cAMP & cGMP) and signalling mediated by $Ca^{2+}$ in response to cellular stimuli [21,22].

Phosphodiesterases have been shown to be further regulated through differential splicing, The PDE1 gene family has a large number of alternatively spliced transcripts. The PDE1, A gene has in total 7 splice variants found in a variety of species. Bovine specific PDE1A1 and 1A2 are homologous, diverging only at their amino termini. All the other PDE1A splice variants are characterised by an insertion of 14 amino acids. Human PDE1A3 [25] and murine PDE1A2 differ from the bovine sequences with alternative carboxy and amino termini respectively. Furthermore, a recent paper by Snyder et.al[40] describes a PCR based cloning strategy which has identified further potential splice variants which differ at both the amino & carboxy termini. To date no splice variants have been identified for PDE1B although four splice variants of the PDE1C gene (differing at both their amino & carboxy termini) have been identified [26]. An example of the functional importance of these alternative splicing events is demonstrated by examining the 5' splice variants of the PDE1A gene. These variants give rise to the 59 kDa PDE1A1 and the 61 kDa PDE1A2 isozymes that have been isolated from bovine heart and brain respectively [11, 12]. Functionally these splice variants change the structure of one of the two CaM binding domains resulting in the PDE1A1 isozyme having a higher affinity for CaM than the PDE1A2 isozyme [12,28,29,34].

We now describe the use of a novel positive cDNA selection technology (GeneTrapper™, Life Technologies Inc, Rockville) to isolate members of the human PDE1 gene family, including alternatively spliced variants, in particular novel sequences thereof. In addition to isolating all previously identified PDE1 subtypes and the majority of their splice variants, we identified two additional PDE1 splice variants. One, PDE1A5 appears to be the direct human orthologue of the 59 kDa bovine PDE1A1. The other PDE1B2, is the first example of an alternative splice variant for the PDE1B gene. We have examined the tissue distribution of these alternatively spliced isozymes in a variety of human tissues using sequence specific probes and demonstrate that tissue specific expression is associated with these sequences.

Materials & Methods.

2.1—Design & Biotinylation of a Degenerate Oligonucleotide for the Isolation of PDE1 Subtypes.

The human PDE1A, B & C (Genbank accession numbers U40370, U56976, U40371) amino acid sequences were aligned using the Clustalw programme [30]. A region of 8 amino acids at position 282-290 in U40370 comprising YNDRSVLE were chosen since these residues are conserved between the three subtypes. An oligonucleotide was designed with 64 fold degeneracy so that the nucleotide sequence of the capture oligonucleotide would encompass all possible 24 mers :5' CWG CWG YAT YCA TGA YTA YGA GC 3'. The oligonucleotide was synthesised by LTI (Life Technologies Ltd, Paisley, Scotland) and PAGE purified. The oligonucleotide was biotinylated using terminal transferase incorporating 14-dCTP as described in the GeneTrapper™ Manual (LTI, Catalogue number 10356-020).

2.2—Isolation of Human PDE1 Subtypes.

Human lung, testis, spleen & foetal brain cDNA libraries were purchased from Life Technologies, Inc (LTI). 100 ml of Luria Broth (10 g tryptone, 5 g yeast extract, 5 g NaCl/liter)+100 ug/ml Ampicillin was inoculated with 2.5× $10^9$ c.f.u of each cDNA library. Each library was grown up & prepared individually. Each culture was grown up overnight at 30° C. and plasmid DNA was prepared as described in the GeneTrapper™ protocol (LTI). Detailed methods for the positive selection of cDNA clones using GeneTrapper™ (LTI) are outlined in the kit protocols, these were strictly followed except for the following modifications. The single stranded cDNA library was combined with 5 ng of biotinylated degenerate oligonucleotide and hybridised at 37° C. for 1 hour. The eluted single stranded DNA was repaired using the degenerate oligonucleotide as a primer for DNA polymerase extension. The repaired cDNA libraries were electroporated in to the *E.coli* strain DH10B (LTI) using the manufacturers protocol.

2.3—Identification of Human PDE1 Subtypes.

The electoporated DH10B *E.coli* containing the selected cDNA libraries were plated out on to Luria Broth agar plates (5 g Tryptone, 10 g yeast extract, 5 g NaCl, 14 g Agar/liter) plus 100 ug/ml Ampicillin and grown overnight at 37° C. The resulting colonies were picked into 96 well microtitre plates containing freezing media (5 g Tryptone, 10 g yeast extract, 5 g NaCl, 6% glycerol) using a Biopick robot (BioRobotics Ltd) and then grown to saturation overnight at 37° C. The colonies were arrayed in duplicate on to a 22 cm×22 cm Hybond N membrane (Amersham) in a 3×3 array using a Biogrid robot (BioRobotics Ltd) and the membranes were incubated on agar overnight at 37° C. Each membrane was processed using standard procedures [31], plasmid DNA was fixed to each membrane using the Stratalinker (Stratagene). Each membrane was hybridised at 50° C. in ExpressHyb (Clontech), with a [$\gamma^{32}$-P]dATP end labelled capture oligonucleotide, labelled using the end terminal labelling kit (LTI catalogue number 38060-018) and 10 μCi [$\gamma^{32}$-P]dATP (Amersham AA0068). The membranes were washed at the hybridisation temperature in 6×SSPE/0.1% SDS, 3×20 mins and then exposed to autoradiographic film (Kodak, Ltd) for 72 h.

The positive clones were identified, picked and grown-up in liquid culture, subsequently plasmid DNA was prepared using Qiagen Kits (Qiagen, East Sussex, UK) and the Qiagen 9600 BioRobot (Qiagen)

2.4—Determination & Computer Analysis of DNA Sequences

DNA sequencing was performed on both strands by fluorescence-tagged dye terminator cycle sequencing (Perkin-Elmer, Norwalk, Conn.) followed by analysis on an ABI 377 DNA sequencer (Applied Biosystems, Foster City, Calif.). Sequence data was analysed by BLAST (Basic Local Alignment Search Tool) searching [32].

2.5—RNA Master Blot and Northern Blot Hybridisation & Probe Generation

RNA master blots and multiple tissue northerns were purchased from Clontech and prehybridised for 1 hour in ExpressHyb hybridisation solution (Clontech) at 55° C. The alternatively spliced amino terminal regions were amplified by PCR using the following primer pairs:-

PDE1A3

-5' CAG TAA CAG ATG AGC TGC 3' (SEQ ID NO:14)
and

5'GTA TTC CTT TCA GGC G 3' (SEQ ID NO:15)

to produce a 159bp fragment.

Primers for PDE1A5 (SEQ ID NO:16)

5' CAC ATT TCC TCT CTG G 3'
and

5' GGG TCT TTG GAG ATG TTT CTT CC 3' (SEQ ID NO:17)

to produce a 107bp fragment.

Primers for PDE1B1

5' CTG AGC ATG GAG CTG TCC 3' (SEQ ID NO:18)
and

5' CAG AGA CCG AAG CTT AAT CC 3' (SEQ ID NO:19)

to produce a 120bp fragment.

Primers for PBE1B2

5' CCA AAG AGG AAG TTG TCC 3' (SEQ ID NO:20)
and

5' GCA GCC TGA CAA TGG 3' (SEQ ID NO:21)

to produce a 144bp fragment.

DNA was labelled using the Megaprime random labelling system (Amersham) using 5 μCi of [$\alpha$-$^{32}$P]dCTP (Amersham AA0005), and then added to fresh Expresshyb and hybridised to the blot overnight at 55° C., with gentle shaking at 50 rpm. Blots were then washed 3× at room temperature for 10 minutes each in 2×SSC (150 mM NaCl, 30 mM Na citrate)/0.1% SDS followed by 2 washes in 0.2×SSC (15 mM NaCl, 3 mM Na citrate)/0.1% SDS at 55° c. for 20 minutes each. Blots were then exposed to autoradiographic film for 72 h. All the blots were subsequently stripped using standard methods and reprobed with β-actin to check for equal loading.

Results & Discussion 3.1—the Isolation of PDE1 Subtypes.

Isoforms of the PDE1 gene family have been implicated in various physiological roles, consequently isolation of novel family members could provide further insight into intracellular cyclic nucleotide metabolism.

We have devised a strategy to isolate as many PDE1 subtypes and splice variants as possible with a view to delineating the PDE1 family of genes. To maximise our chances of isolating new PDE1 subtypes we chose 4 cDNA libraries from a diverse range of human tissues, namely lung, testis, spleen & foetal brain. These were screened individually to ensure that we would have the best chance of isolating rare transcripts. A degenerate oligonucleotide designed from an alignment of the three known PDE1 subtypes, (FIG. 1) was used in conjunction with the positive cDNA selection kit (GeneTrapper™, LTI) to isolate PDE1 enriched cDNA libraries. Each enriched library was arrayed and probed with the degenerate oligonucleotide to identify those clones that contained a sequence homologous to the capture oligonucleotide. Sequence analysis of the 5' end of all the positive clones showed that the selection process was successful with over 50% of the clones sequenced being one of the PDE1 subtypes (Table 1). This is the first example of multiple gene family members being isolated using a single redundant oligonucleotide with this type of technology.

TABLE 1

DNA sequence analysis of the GeneTrapper ™ selected cDNA libraries

| Library Screened | Number of positive clones identified by hybridisation | Number of PDE1A clones present by sequencing (27) | Number of PDE1B clones present by sequencing (14) | Number of PDE1C clones present by Z1sequencing (11) |
|---|---|---|---|---|
| Foetal brain | 378 | 52 | 226 | 32 |
| Lung | 72 | 13 | 13 | 17 |
| Spleen | 10 | 6 | — | — |
| Testis | 36 | 14 | 6 | 2 |

The above table details the cDNA libraries that have been screened using a single degenerate oligonuclotide. The second column describes the number of clones that hybridised to the radiolabelled degenerate oligonuclotide. The remaining columns detail the number of PDE1 subtypes identified by DNA sequencing. The number in brackets represents the number of individual clones present in each library.

The selection process uses an amplified cDNA library, therefore, the absolute number of clones isolated from each library can be misleading and will not truly reflect transcript expression levels. To obtain a more accurate measurement of truly independent clones in each library a Java applet was designed to allow the rapid alignment of all the sequences generated to identify those clones which had multiple copies, indicated by a common 5' end. An example of the output of the programme for the PDE1B clones is given in FIG. 2. A single representative of each independent clone was picked and the full length sequence was determined. Using this approach several isoforms of PDE1A, 1B and 1C were isolated, although no new PDE1 subtypes were identified suggesting, although not definitively proving, that there are only three human PDE1 genes.

3.2—Identification of N-terminal Splice Variants for PDE1 Subtypes.

FIG. 3 gives a schematic alignment of the previously known PDE1A splice variants. The variant labelled mouse PDE1A4 corresponds to sequence assession number U56649 and is annotated as PDE1A2. However, this sequence does contain an insertion of 14 amino acids relative to the bovine PDE1A2 and an additional 20 amino acids at the amino terminus, we suggest that this variant be renamed PDE1A4 to bring it in line with current nomenclature [33].

Sequence analysis of the human PDE1A clones identified two variants. The first was identical to the known human PDE1A3, the second was identical to PDE1A3 except for the substitution of 34 amino terminal residues by an alternative 18 residues (FIG. 4A). We have named our clone PDE1A5. The full length cDNA encodes a protein of 519 amino acids with a predicated molecular mass of 59.6 kDa. The sequence data identifies multiple stop codons in all 3 reading frames upstream of the putative initiator methionine. The PDE1A5 protein sequence contains residues that are identical to a calmodulin binding region identified in the 59 kDa bovine PDE1A1 and it also contains a region of 250 amino acids conserved in all mammalian PDEs that corresponds to the catalytic domain [7–10]. Although PDE1A5 is identical with a 5' RACE product identified by Snyder et.al. [40] and most similar to the bovine PDE1A1, the full length human protein contains two regions that are not found in the bovine protein. One region is a 14 amino acid insertion in the human protein following amino acid 443. The second region is in the C terminus; the human C terminal 14 amino acids has no homology to the C terminal 23 amino acids of the bovine protein. These observations mirror the comparison between the bovine PDE1A2 and human PDE1A3 [25] suggesting that these two regions are in fact species dependant, this is schematically summarised in FIG. 3. To support this hypothesis none of the 27 independent clones sequenced contained the 14 amino acid deletion seen in the bovine PDE1A gene.

PDE1B1 is the only version of PDE1B gene that has been previously identified in human, bovine, mouse and rat (U56976,M94867,L01695 & M94537). Sequence analysis of the 14 independent clones identified two variants, the first PDE1B1 and the second a novel variant differing at the amino terminus through substitution of 38 residues with an alternative 18 residues (FIG. 4B). This is the first example of a splice variant of the PDE1B gene and has been named PDE1B2. Interestingly the divergent 18 amino acid stretch shows homology to PDE1A1 amino terminal region (FIG. 4C). It has already been shown that the amino termini of PDE1B1 and PDE1A2 share close homology (FIG. 4D) and that this may account for the similarity in CaM binding affinity between these isozymes [34]. Without wishing to be bound by theory it may be interesting to speculate upon the significance of the homology between the amino termini of PDE1B2 & PDE1A1 suggesting that this too may lead to similar CaM binding affinity. Following these observations it would suggest that PDE1B2 may have at least a 10 fold higher affinity for CaM than PDE1B1.

The full length PDE1B2 cDNA encodes a protein of 516 amino acid with a predicted molecular weight of 59 kDa. The sequence data shows multiple stop codons in all 3 reading frames upstream of the putative initiator methionine. The protein sequence contains residues that are identical to the calmodulin binding regions and the conserved catalytic domain as identified in the PDE1B1 sequence [23, 27, 34].

3.3—Comparative Tissue Distribution of the PDE1A & 1B Subtypes.

Alignment of the protein sequences for the PDE1A isozymes identifies two amino terminal regions formed by alternative splicing events. To compare the expression profile of these two regions, they were isolated by PCR, radiolabelled and used to probe an RNA master blot (data not shown) and five multiple tissue northern blots (FIG. 5). The strongest signal for PDE1A3 is observed in the brain, specifically, occipital lobe, cerebellum, temporal lobe, acumens & foetal brain. In contrast, PDE1A5 has the strongest signal from thyroid gland but at lower levels in adult & foetal kidney. Most interestingly no expression is detectable in any brain region. The physiological role of PDE1A5 is not known, but it may play a pivotal role in the physiological regulation of thyroid function. The action of thyroid stimulating hormone on its cell surface receptor in the thyroid has been shown to activate adenylate cyclase [35,36] and phosphodiesterase activity has previously been detected in the thyroid gland [37,38]. Therefore, PDE1A5 as well as other phosphodiesterases expressed in the thyroid gland[39], may modulate the action of this hormone.

Likewise, a comparative analysis using the two alternatively spliced amino terminal regions of PDE1B was performed. The strongest signals for PDE1B1 were detected in the brain, in particular in the caudate nucleus and putamen as previously reported [27]. Lower levels of signal were observed in other brain regions and no significant signals were obtained from peripheral tissues. In contrast, PDE1B2 showed strongest signal levels in spinal cord. Lower signal levels were observed from thyroid, thymus, uterus, small intestine, putamen and caudate nucleus and totally absent from other brain regions (FIG. 5).

All our data were confirmed by independent RNA master blot & Northern blot experiments and in each case there was no cross-hybridisation with the PDE1A3, A5, 1B1 & 1B2 dot blot standards included with the samples.

The data we have described is an example of PDE1A & PDE1B isozymes showing tissue specific distribution as a direct result of the alternatively spliced amino termini. This suggests that expression of these PDE isozymes is under the control of different splicing mechanisms. The two isozymes of the PDE1A and 1B gene are produced by differential exon usage resulting in both having identical kinetic parameters and specificity for cyclic nucleotides but potentially different affinities for CaM. Therefore, this would allow differential regulation by $Ca^{2+}$/CaM cellular signals in a tissue specific manner.

During the preparation of this manuscript Snyder et.al. [40] published data validating the existence of the PDE1A5 amino terminal splice variant. Interestingly, the authors performed a kinetic analysis comparing PDE1A3, A5 and two further potential splice variants which were not identified in our study. There was no significant difference in the Km of the splice variant isozymes, suggesting that differential amino splicing of PDE1A's does not confer changes in enzymatic activity but rather as suggested above they may cause alterations in mode of regulation.

In summary, we have used a novel positive cDNA selection technique to isolate all the members of the human PDE1 gene family. As well as showing that the cDNA selection technique has a unique application in being able to rapidly isolate entire target gene families. Our data suggests that we may have come to closure for the number of human PDE1 genes, although as suggested by Snyder et.al. [40] further PDE1A splice variants may remain to be identified and characterised. We have isolated two novel splice variants PDE1A5, 1B2 and have shown by comparative expression analysis that these splice variants are differentially expressed and they may also be differentially regulated by their altered sensitivity to Ca2+/CaM. This suggests that PDE1 splice variants may be fulfilling alternate physiological roles depending on the local cellular environment.

Baculovirus Expression

The following studies demonstrate that the PDE enzyme of the present invention—called PDE here for short—can be generated using a baculovirus expression system.

The following studies also demonstrate that the PDE shows cyclic nucleotide hydrolytic activity when it has been expressed in the baculovirus system.

The PDE enzyme was generated using the baculdvirus expression system based on *Autographa californica* nuclear polyhedrosis virus (AcNPV) infection of *Spodoptera frugiperda* insect cells (Sf9 cells).

In these studies, cDNA encoding PDE was cloned into the donor plasmid PFASTBAC-FLAG which contains a mini-Tn7 transposition element. The recombinant plasmid was transformed into DH10BAC competent cells which contain the parent bacmid bMON14272 (AcNPV infectious DNA) and a helper plasmid. The mini-Tn7 element on the pFASTBAC donor can transpose to the attTn7 attachment site on the bacmid thus introducing the PDE gene into the viral genome. Colonies containing recombinant bacmids are identified by disruption of the lacZ gene. The PDE/bacmid construct can then be isolated and infected into insect cells (Sf9 cells) resulting in the production of infectious recombinant baculovirus particles and expression of recombinant PDE-FLAG fusion protein.

The phosphodiesterase activity of the crude cell extracts was measured.

Cells were harvested and extracts prepared 24, 48 and 72 hours after transfection.

These results confirm that PDE cDNA encodes a phosphodiesterase which is able to hydrolyse cAMP and/or cGMP.

The crude lysate material was purified by FPLC using a column containing agarose beads (M2 affinity gel) to which a purified $IgG_1$ monoclonal anti-FLAG antibody had been conjugated by hydrazide linkage (Eastman Kodak). This allows the specific retention on the column of the recombinant material (since this is fused to the FLAG epitope) whilst the endogenous insect proteins are washed off in the eluate. The recombinant material is then washed off under conditions of low pH. This purified material was more suitable for detailed enzymatic and inhibitor studies. The purity of the material is assessed by coomassie staining after sodium dodecyl sulphate-polyacrylamide gel electrophoresis (SDS-PAGE) or through western blotting onto a nitro-cellulose membrane of an unstained SDS-PAGE (containing recombinant PDE) and analysis with the IgG1 monoclonal anti-FLAG epitope antibody. The PDE-FLAG fusion protein is detected due to the interaction between the anti-FLAG antibody and the FLAG epitope which is fused to the PDE protein.

The phosphodiesterase activity of the purified PDE-FLAG fusion protein was assayed using a commercially available SPA (scintillation proximity assay) kit (Amersham—Amersham place, Little Chalfont, Bucks, HP7 9NA UK) for either cAMP and/or cGMP hydrolytic activity. This can be used to permit the determination of the Km value for PDE cAMP and/or cGMP by determining the enzyme activity at a range of substrate concentrations allowing the calculation of an approximate Vmax value for the enzyme.

The results of these experiments show that the PDE cDNA encodes a phosphodiesterase which is able to hydrolyse cAMP and/or cGMP.

SUMMARY

A novel cDNA selection technique has been used to isolate full length human cDNAs encoding members of the PDE1 calcium-calmodulin regulated phosphodiesterase gene family. This analysis resulted in the isolation of cDNAs representing multiple splice variants of PDE1A, 1B & 1C from a variety of tissues. Included among these were two novel splice variants for PDE1A & 1B. The first, PDE1A5 encodes a 519 amino acid protein which is different from the bovine PDE1A1 by the insertion of 14 amino acids, thereby producing a divergent carboxy terminus and differing from human PDE1A3 through a divergent amino terminus. The second example represents the first occurrence of a splice variant of the PDE1B gene. PDE1B2 encodes a 516 amino acid protein and diverges from PDE1B1 by the replacement of the first 38 amino acids by an alternative 18 amino acids.

We have used the splice variant sequence differences in order to perform studies to examine differential tissue expression by northern analysis. PDE1A3 was shown to be restricted to subregions of the brain whilst PDE1A5 was relatively highly expressed in the thyroid gland and not in subregions of the brain. Northern analysis revealed that PDE1B1 is exclusively expressed in the brain, whereas PDE1B2 is expressed in more peripheral tissues such as spinal cord and small intestine.

In summary the present invention provides and the Examples show inter alia:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

1. Beavo, J. A. (1995) *Physiol. Rev* 75, 725–748
2. Manganiello V. C., Murata T., Taira M., Belfrage P.,& Degerman E. (1995) *Archiv. Biochem. Biophys.* 322, 1–13.
3. Soderling, S. H., Bayuga, S. J., & Beavo, J. A. (1998) *J. Biol. Chem.* 273, 15553–15558.
4. Fisher, D. A., Smith, J. F., Pillar, J. S., St Denis, S. H., & Cheng, J. B (1998) *J. Biol. Chem* 273, 15559–155564.
5. Soderling S. H., Bayuga S. J. & Beavo J. A. (1998) *Proc. Natl. Acad. Sci. USA,* 95, 8991–8996.
6. Fujishige K., Kotera J., Michibata H., Yuaga K., Takebayashi S. I., Okumura K., & Omori K. (1999) *J. Biol. Chem,* 274, 18438–18445.
7. Charbonneau H. (1990) *Mol. Pharmacol.Cell.Regul.* 2, 267–296.
8. Jin S. L., Swinnen J. V., & Conti M. (1992) *J. Biol.Chem.* 267, 18929–18939.
9. Pillai R., Kytle K., Reyes A., & Colicelli J. (1993) *Proc. Natl. Acad. Sci. USA* 90 11970–11974.
10. Pillai R., Staub S. F., & Colicelli J. (1994) *J. Biol. Chem.* 269, 30676–30681.
11. Novack J. P., Charbonneau H., Bently J. K., Walsh K. A. & Beavo J. A. (1991) *Biochemistry.* 30, 7940–7947.
12. Sonnenburg W. K., Seger D., Kwak K. S., Huang J., Charbonneau H. & Beavo J. A. (1995) *J. Biol. Chem.* 270, 30989–31000.
13. Stroop S. D. & Beavo J. A. (1992) *Adv. Second Messenger Phosphoprotein Res.* 25, 55–71.
14. Kincaid R. L., Stith-Coleman T. E. & Vaughan M. (1985) *J. Biol. Chem.* 260, 9009–9015.
15. Charbonneau H., Kumar S., Novack J. P., Blumenthal D. K., Griffen P. R., Shabanowitz J., Hunt D. F., Beavo J. A. & Walsh K. A. (1991) *Biochemistry.* 30, 7931–7940.
16. Sharma R. K. (1991) *Biochemistry.* 30, 5963–5968.
17. Sharma R. K. & Wang J. H. (1985) *Proc. Natl. Acad. Sci. USA,* 82 2603–2607.
18. Hashimoto Y., Sharma R. K. and Soderling T. R. (1989) *J. Biol. Chem.* 264, 10884–10887.
19. Zhang G. Y., Wang J. H. & Sharma R. K. (1993) *Mol. Cell. Biochem.* 122, 159–169.
20. Sharma R. K. & Wang J. H. (1986) *Biochem. Cell. Biol.* 64, 1072–1080.
21. Wang J. H., Sharma R. K. & Mooiborek M. J. (1990) *Mol. Pharmacol. Cell Regul.* 2, 19–59.
22. Sonnenburg W. K. & Beavo J. A. (1994) *Adv. Pharmacol.* 26, 87–114.
23. Bentley J. K., Kadlecek A., Sherbert C. H., Seger D., Sonnenburg W. K., Charbonneau H., Novack J. P. & Beavo J. A. (1992) *J. Biol Chem.* 267 18676–18682.
24. Sonnenburg W. K., Seger D. & Beavo J. A. (1993) *J.Biol.Chem* 268, 645–652.
25. Loughney K., Martins T. J., Harris E. A. S., Sadhu K., Hicks J. B., Sonnenburg W. K., Beavo J. A. & Ferguson K. (1996) *J. Biol Chem.* 271, 796–806.
26. Yan C., Zhao A. Z., Bentley J. K., Loughney K., Ferguson K. & Beavo J. A. (1995) *Proc. Natl. Acad. Sci. USA* 92, 9677–9681.
27. Polli J. W. & Kincaid R. L. (1992) *Proc.Natl.Acad.Sci. USA* 89, 11079–11083.
28. Hansen R. S & Beavo J. A. (1986) *J. Biol Chem.* 261, 14636–14645.
29. Sharma R. K. (1995) *Molecular and Cell. Biochem.* 149/150, 241–247
30. Thompson J. D., Higgins D. G. & Gibson T. J. (1994) *Nucleic Acid Res.* 22, 4673–4680.
31. Maniatis T., Fritsch E. F. & Sambrbok J. (1982) *Molecular Cloning: A laboratory manual* (Cold Spring Harbour Lab., Cold Spring Harbour, N.Y.).
32. Altshul S. F, Gish W., Miller W., Meyers E. W. & Lipman D. J. (1990) *J. Mol. Biol.* 215, 403–410.
33. Beavo J. A., Conti M. & Heaslip R. J. (1994) *Molec. Pharmacol.* 46, 399–405.
34. Novack J. P, Charbonneau H., Bentley K., Walsh K. A. and Beavo J. A. (1991) *Biochemistry.* 30, 7940–7947.
35. Pastan I. & Katzen R., (1967) *Biochem. Biophys. Res. Commun.* 29, 792.
36. Zor U., Kaneko T., Lowe I. P., Bloom G. & Field J. B. (1969) *J. Biol Chem.* 244, 5189
37. Nagasaka A. & Hidaka H. (1980) *J. Clin. Endocrinol. Metab.* 50, 726–733.
38. Yagura T. Nagata I., Kuma K. & Uchino H. (1985) *J. Clin. Endocrinol. Metab.* 60 1180–1186.
39. Hayash M., Matsushima K., Ohash H., Tsunoda H., Murase S., Kawarda Y. & Tanaka T. (1998) *Biochem. Biophys. Res. Commun.* 250, 751–756. Snyder P. B., Florio V. A., Ferguson K. & Loughney K. (1999) *Cell. Signal.* 11, 535–544.

The invention claimed is:

1. An isolated or purified amino acid sequence selected from the group consisting of:
   (a) an amino acid sequence set forth as SEQ ID NO: 1;
   (b) an amino acid sequence having greater than 98% sequence identity to SEQ ID NO: 1, said sequence having phosphodiesterase (PDE or PDE1B2) activity and;
   (c) an amino acid sequence of SEQ ID NO: 1, comprising amino acids 1–24 of SEQ ID NO:1.

2. An assay method for identifying an agent that can affect PDE1B2 activity or expression, the assay method comprising
   contacting an agent with an amino acid according to claim 1 or a nucleotide sequence according to any one of claims 2 to 7; and
   measuring the activity or expression of PDE1B2;
   wherein a difference between a) PDE activity or expression in the absence of the agent and b) PDE activity or expression in the presence of the agent is indicative that the agent can affect PDE1B2 activity or expression.

3. An isolated or purified phosphodiesterase capable of having an immunological reaction with an antibody raised against the amino acid sequence(s) of claim 1.

4. An isolated phosphodiesterase wherein the phosphodiesterase is expressed from a nucleotide sequence obtainable from NCIMB 41026 and having the sequence of SEQ ID NO: 2.

5. An isolated recombinant phosphodiesterase as set forth in claim 1.

6. The isolated or purified amino acid sequence of claim 1 comprising SEQ ID NO:1.

7. The isolated or purified amino acid sequence of claim 1 comprising an amino acid sequence having greater than 98% sequence identity to SEQ ID NO: 1, said amino acid sequence having phosphodiesterase activity.

8. The isolated or purified amino acid sequence of claim 1 comprising an amino acid sequence including amino acids 1–24 of SEQ ID NO:1.

* * * * *